US010130650B2

United States Patent
Huang et al.

(10) Patent No.: US 10,130,650 B2
(45) Date of Patent: Nov. 20, 2018

(54) COMPOSITIONS AND METHODS FOR TREATING AUTOIMMUNE AND INFLAMMATORY DISEASES

(71) Applicants: The Children's Hospital of Philadelphia, Philadelphia, PA (US); Trustees of the University of Pennsylvania, Philadelphia, PA (US)

(72) Inventors: Yanping Huang, Drexel Hill, PA (US); Janis K. Burkhardt, Ardmore, PA (US); Taku Kambayashi, Malvern, PA (US)

(73) Assignees: The Children's Hospital of Philadelphia, Philadelphia, PA (US); The Trustees of The University of Pennsylvania, Philadelphia, PA (US)

(*) Notice: Subject to any disclaimer, the term of this patent is extended or adjusted under 35 U.S.C. 154(b) by 0 days.

(21) Appl. No.: 15/114,572

(22) PCT Filed: Jan. 27, 2015

(86) PCT No.: PCT/US2015/013069
§ 371 (c)(1),
(2) Date: Jul. 27, 2016

(87) PCT Pub. No.: WO2015/113041
PCT Pub. Date: Jul. 30, 2015

(65) Prior Publication Data
US 2016/0339053 A1 Nov. 24, 2016

Related U.S. Application Data

(60) Provisional application No. 61/931,984, filed on Jan. 27, 2014.

(51) Int. Cl.
| | | |
|---|---|---|
| *A61K 31/713* | (2006.01) | |
| *A01K 67/027* | (2006.01) | |
| *C12N 15/113* | (2010.01) | |
| *A61K 35/17* | (2015.01) | |
| *A61K 35/28* | (2015.01) | |
| *A61K 45/06* | (2006.01) | |
| *A61K 35/12* | (2015.01) | |

(52) U.S. Cl.
CPC ........ *A61K 31/713* (2013.01); *A01K 67/0276* (2013.01); *A61K 35/17* (2013.01); *A61K 35/28* (2013.01); *A61K 45/06* (2013.01); *C12N 15/113* (2013.01); *A01K 2217/075* (2013.01); *A01K 2217/15* (2013.01); *A01K 2217/206* (2013.01); *A01K 2227/105* (2013.01); *A01K 2267/0387* (2013.01); *A61K 2035/124* (2013.01)

(58) Field of Classification Search
None
See application file for complete search history.

(56) References Cited

U.S. PATENT DOCUMENTS

| | | |
|---|---|---|
| 2004/0067220 A1 | 4/2004 | Sykes |
| 2005/0119163 A1 | 6/2005 | Burke et al. |
| 2007/0249048 A1 | 10/2007 | Dai et al. |
| 2011/0118337 A1* | 5/2011 | Chau .................... C12N 15/113 514/44 A |
| 2011/0189095 A1 | 8/2011 | Arap et al. |

FOREIGN PATENT DOCUMENTS

| | | |
|---|---|---|
| WO | 01/25405 | 4/2001 |
| WO | 2009/076551 | 6/2009 |

OTHER PUBLICATIONS

Gu, J.J., et al., "Abl Family Kinases Modulate T Cell-Mediated Inflammation and Chemokine-Induced Migration Through a HEF1-Rap1 Signaling Module" Sci. Signal. (2012) 5(233):ra51.
Rodrigues, S.P., et al., "Crkl and Crkll Function as Key Signaling Integrators for Migration and Invasion of Cancer Cells" Mol. Cancer Res. (2005) 3(4):183-94.
Huang, Y., et al., "CRK proteins selectively regulate T cell migration into inflamed tissues" J. Clin. Invest. (2015) 125(3)1019-32.
Peterson, A.C., et al., "T cell development and function in CrkL-deficient mice" Eur. J. Immunol. (2003) 33(10):2687-95.
Park, T.J., et al., "Crk and Crk-Like Play Essential Overlapping Roles Downstream of Disabled-1 in the Reelin Pathway" J. Neurosci. (2008) 28(50):13551-62.
Nolz, J.C., et al., "The WAVE2 complex regulates T cell receptor signaling to integrins via Abl- and CrkL-C3G-mediated activation of Rap1" J. Cell. Biol. (2008) 182(6):1231-44.
Zhang, W., et al., "Negative Regulation of T Cell Antigen Receptor-mediated Crk-L-C3G Signaling and Cell Adhesion by Cbl-b" J. Biol. Chem. (2003) 278(26):23978-83.
Reshef, R., et al., "Blockade of Lymphocyte Chemotaxis in Visceral Graft-versus-Host Disease" N. Engl. J. Med. (2012) 367(2):135-45.
Huang, Y., et al., "The c-Abl tyrosine kinase regulates actin remodeling at the immune synapse" Blood (2008) 112(1):111-9.
Birge, R.B., et al., "Crk and CrkL adaptor proteins: networks for physiological and pathological signaling" Cell. Commun. Signal. (2009) 7:13.
Huang, Y., et al., "CRK/CRKL proteins regulate T cell migration and activation (P5104)" J. Immunol. (2013) 190 (1 Supplement):58.6.
Bouchlaka, M.N., et al., "Immunotherapy following hematopoietic stem cell transplantation: potential for synergistic effects" Immunotherapy (2010) 2(3):399-418.
Gelkop, S., et al., "Involvement of crk adapter proteins in regulation of lymphoid cell functions" Immunol. Res. (2003) 28(2):79-91.
Huang, Y., et al., "The adaptor proteins Crk and CrkL regulate T cell adhesion and selectively promote migration to sites of inflammation" Mol. Biol. Cell (2014) 25:P2190.

(Continued)

*Primary Examiner* — J. E. Angell
(74) *Attorney, Agent, or Firm* — Robert C. Netter, Jr.; Dann, Dorfman, Herrell & Skillman

(57) ABSTRACT

Compositions and methods are provided for the treatment and/or prevention of an inflammatory and/or autoimmune disease or disorder.

17 Claims, 25 Drawing Sheets

Figure 1A:
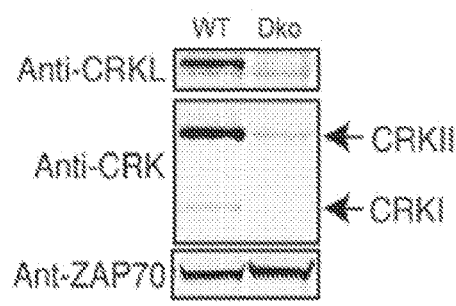

Specification includes a Sequence Listing.

(56) References Cited

OTHER PUBLICATIONS

Colotta, F., et al., "Cancer-related inflammation, the seventh hallmark of cancer: links to genetic instability" Carcinogenesis (2009) 30:1073-1081.
Liu, D. "The adaptor protein Crk in immune response" Immunol. Cell Biol. (2014) 92(1): 80-89.

* cited by examiner

COMPOSITIONS AND METHODS FOR TREATING AUTOIMMUNE AND INFLAMMATORY DISEASES

This application is a § 371 application of PCT/US2015/013069, filed Jan. 27, 2015, which claims priority under 35 U.S.C. § 119(e) to U.S. Provisional Patent Application No. 61/931,984, filed Jan. 27, 2014. The foregoing applications are incorporated by reference herein.

This invention was made with government support under grant no. K01 AR057577 awarded by the National Institutes of Health. The government has certain rights in the invention.

FIELD OF THE INVENTION

The present invention relates to cancer immunotherapy, particularly involving allogeneic hematopoietic stem cells transplants, and treating and/or preventing autoimmune and inflammatory diseases. Specifically, the instant invention provides compositions and methods for the treatment and/or prevention of graft versus host disease.

BACKGROUND OF THE INVENTION

T cells continuously recirculate to perform immune surveillance and effector functions. Within lymph nodes, naive T cells extravasate preferentially through high endothelial venules (HEVs) to survey dendritic cells for foreign antigens. If they fail to encounter cognate antigens, they recirculate to the blood via the efferent lymph. If they encounter cognate antigens, T cells undergo clonal expansion and changes in receptor expression that allow trafficking to first-barrier organs (e.g., skin or the gut mucosa), which they reach by crossing postcapillary venules (Masopust et al. (2013) Nat. Rev. Immunol., 13:309-320). Transendothelial migration involves multiple steps: selectin-mediated rolling, chemokine-triggered integrin activation and consequent firm adhesion, migration along the endothelial wall, and passage through the endothelial barrier (Ley et al. (2007) Nat. Rev. Immunol., 7:678-689). Each step is tightly regulated by membrane receptors on the T cell and the interacting endothelial cells. Chemokine receptors play a pivotal role, triggering rapid changes in T cell adhesion and cytoskeletal remodeling. Although crucial for adaptive immune responses to invading pathogens, T cell migration into peripheral tissues can also lead to inflammation and tissue destruction. For example, in patients receiving allogeneic bone marrow transplants, infiltration of donor T cells leads to graft-versus-host disease (GVHD), a life-threatening complication (Blazar et al. (2012) Nat. Rev. Immunol., 12:443-458). Thus, molecules that regulate T cell tissue infiltration are important therapeutic targets.

Graft versus host disease is a significant problem in patients receiving hematopoietic stem cell transplants, including patients with primary immunodeficiencies, Fanconi anemia, leukemia and lymphoma. This is particularly important for patients receiving allogeneic stem cells to fight leukemia, as these cells are by definition reactive to host tissues. GVHD is a major problem for allogeneic hematopoietic stem cell transplant, occurring with varying degree of severity in 30-70% of patients. Traditional approaches to prevention involve T cell depletion and immunosuppression. T cell depletion is achieved either by ex vivo manipulation of the donor graft (CD34+ selection or CD3+ depletion) or by administering T-cell depleting medications to the recipient (e.g., anti-thymocyte globulin, alemtuzumab). Currently, the combination of a calcineurin inhibitor (e.g., cyclosporine or tacrolimus) and methotrexate is the standard of care for GVHD prevention (Reshef, R. (2012) Clin. Adv. Hematol. Oncol., 10:663-5; Li et al. (2009) Immunotherapy 1:599-621).

The challenge for allogeneic stem cell transplantation is to reduce morbidity from GVHD while maintaining an efficient GVL response and supporting adequate recovery of the immune system. The problem with current strategies is that they affect both GVHD and GVL. Although T cell depletion can be effective in decreasing the rate of GVHD in some subjects, patients have a higher risk for disease relapse due to loss of the GVL response, which is also mediated at least in part by T cells. Thus, this strategy is not suitable for many patients. Similar concerns apply to treatment with immunosuppressive agents, and for many if not all of the novel approaches under development.

SUMMARY OF THE INVENTION

In accordance with one aspect of the instant invention, methods for inhibiting, treating, and/or preventing an autoimmune and/or inflammatory disease or disorder in a subject are provided. The methods comprise the administration of an inhibitor of Crk (CrkI and/or CrkII) and/or CrkL. In a particular embodiment, the methods comprise the administration of a composition comprising an inhibitor of Crk (CrkI and/or CrkII) and/or CrkL and at least one pharmaceutically acceptable carrier. The inhibitors may be delivered to the subject by being delivered to cells prior to delivery to the subject. In a particular embodiment, the methods further comprise the administration of at least one other anti-inflammatory and/or immunosuppressant. In a particular embodiment, the disease or disorder being treated is graft versus host disease. In a particular embodiment, the method comprises administering an inhibitor of Crk and an inhibitor of CrkL, wherein the inhibitors may be the same compound or agent.

BRIEF DESCRIPTIONS OF THE DRAWING

Figure 1B:
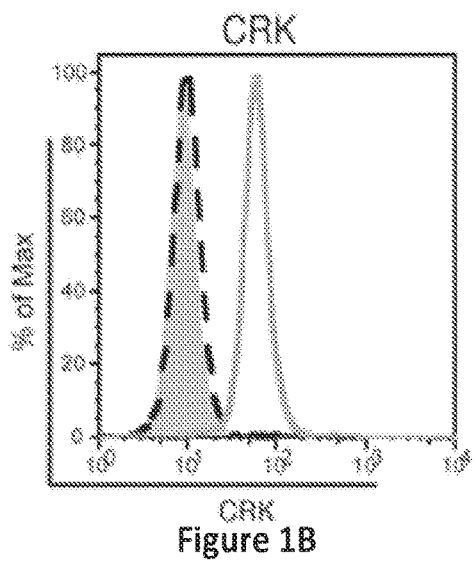
Figure 1C:
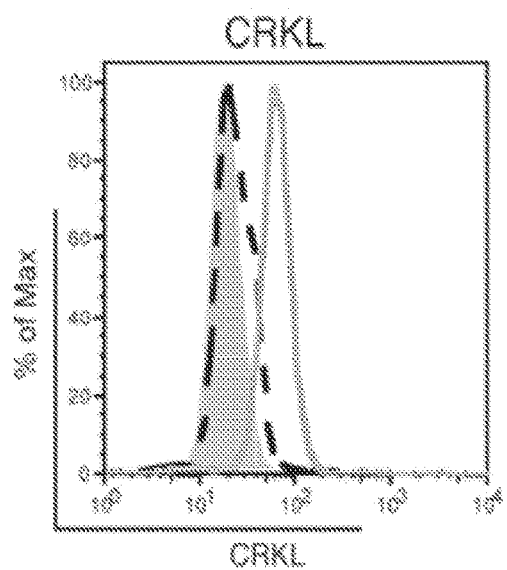
Figure 1D:
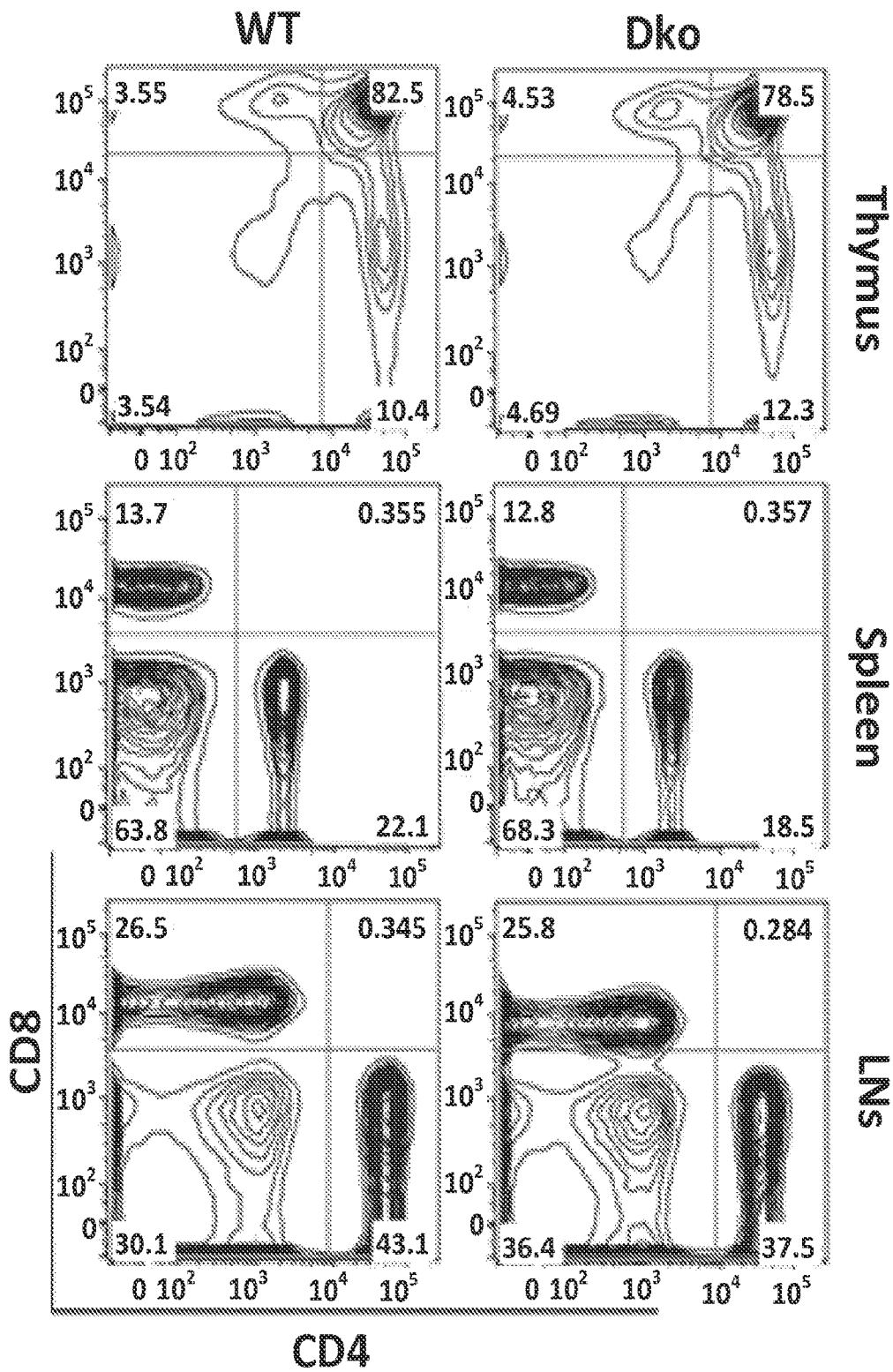
Figure 1E:
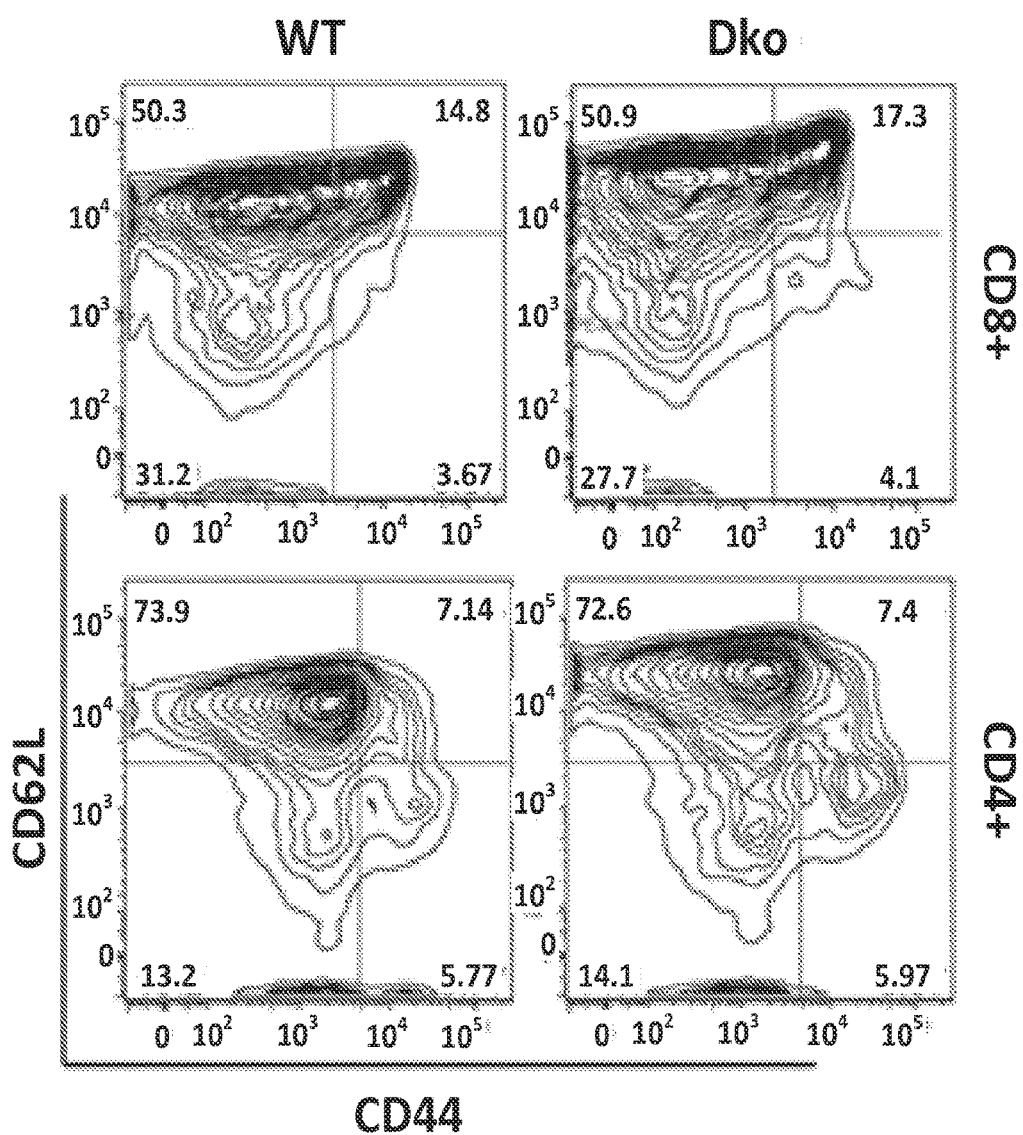

FIGS. 1A-1E show that Crk and Crkl are deleted in T cells of CRK/CRKL Dko mice. CD4$^+$ T cells were purified from lymph nodes of CRK/CRKL Dko and WT mice. Preactivated T cells were prepared by stimulating with plate-bound anti-CD3 and anti-CD28 for 2 days and culturing without stimuli for an additional 5 days. Whole cell lysates were analyzed by SDS-PAGE and immunoblotted with anti-CRKL, anti-CRK, and anti-ZAP70 (FIG. 1A). Preactivated CD4$^+$ T cells were fixed and permeabilized, and the intracellular staining of CRK (FIG. 1B) and CRKL (FIG. 1C) was determined by flow cytometry. Shaded: isotype control; Solid line: WT; Dashed line: Dko. Thymus, spleens, and lymph nodes (LNs) were isolated from WT and CRK/CRKL Dko mice. Single-cell suspensions were analyzed by flow cytometry using the indicated antibodies (FIG. 1D). Gated CD4$^+$ and CD8$^+$ T cells from lymph nodes (mixed peripheral and mesenteric lymph nodes) were analyzed for the indicated surface markers (FIG. 1E).

Figure 2A:
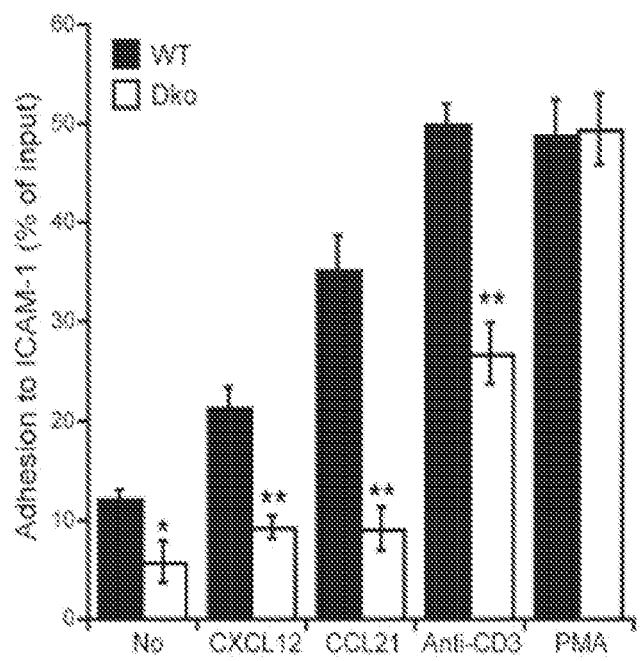
Figure 2B:
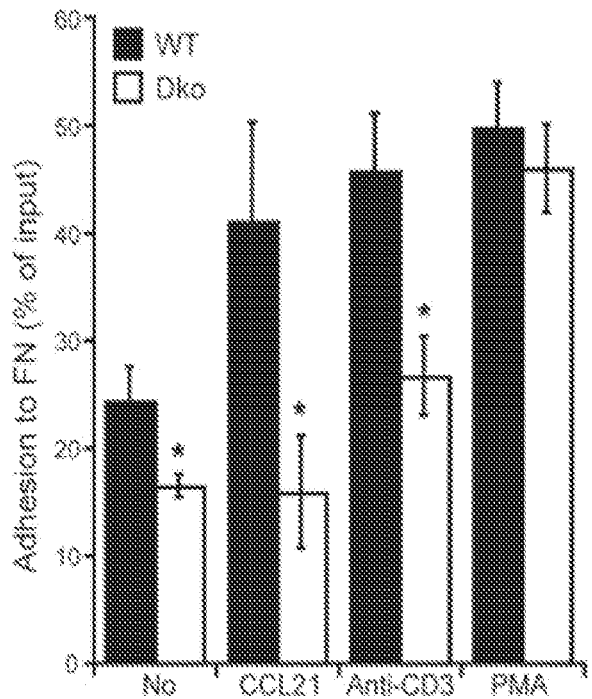
Figure 2C:
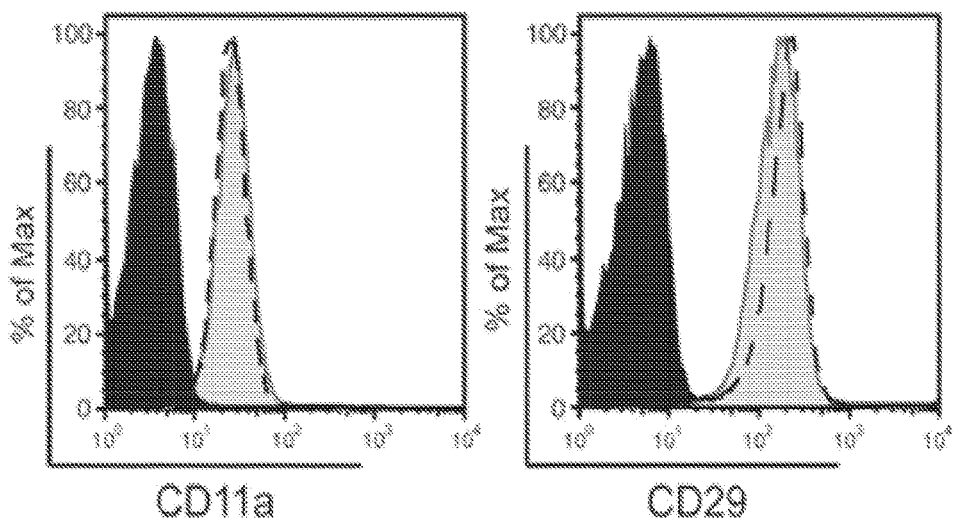
Figure 2D:
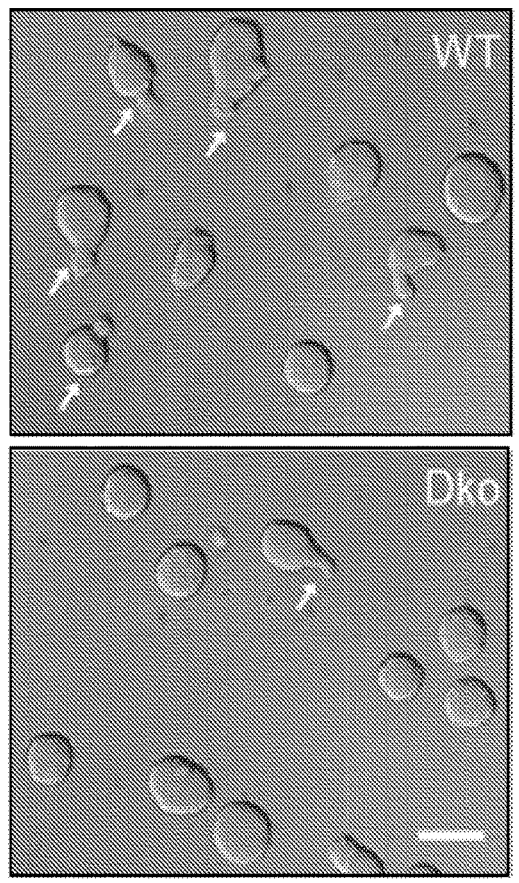
Figure 2E:
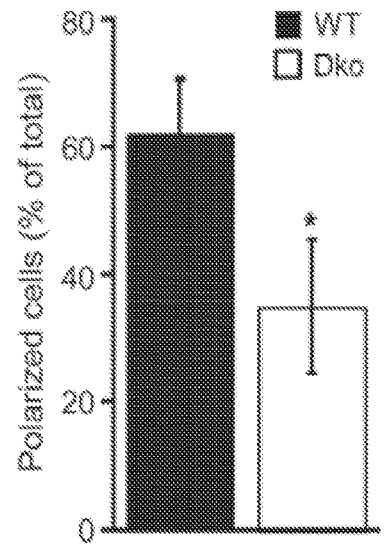

FIGS. 2A-2E show that CRK/CRKL-deficient T cells show defects in integrin-dependent adhesion and polarity induced by integrin engagement. Ninety six-well plates were coated with 1 µg/ml recombinant mouse ICAM-1 (FIG. 2A) or 3 µg/ml fibronectin (FN; FIG. 2B). Preactivated WT and CRK/CRKL Dko CD4$^+$ T cells were stained with calcein-AM, applied to ICAM-1- or fibronectin-coated plates, and allowed to warm to 37° C. for 10 minutes in the presence of 10 nM CXCL12, 10 nM CCL21, 1 μg/ml anti-CD3, or 10 ng/ml PMA. Unbound cells were washed off, and adherent cells were quantified using a fluorescence microplate reader. Data represent averages±SD of triplicate samples from 1 experiment, representative of 5 separate experiments. *P<0.05, **P<0.01. Preactivated WT and CRK/CRKL Dko CD4+ T cells were stained with anti-CD11a-FITC or anti-CD29-PE and analyzed by flow cytometry (FIG. 2C). Black shaded: isotype control: Gray shaded: WT; Dashed line: Dko. Representative data from 3 experiments are shown. To assess polarity responses in those T cells that do bind integrin ligands, preactivated WT and CRK/CRKL Dko CD4+ T cells were applied to fibronectin-coated coverslips. After incubation at 37° C. for 30 minutes, cells were fixed and analyzed by differential interference contrast (DIC) microscopy (FIG. 2D). Arrows indicate polarized T cells with a clear uropod. Cell polarity was also quantified (FIG. 2E). Data are average±SD values from 3 experiments, totaling 433 cells for WT and 387 for CRK/CRKL Dko. *P<0.05. Scale bar: 20 μm.

Figure 3A:
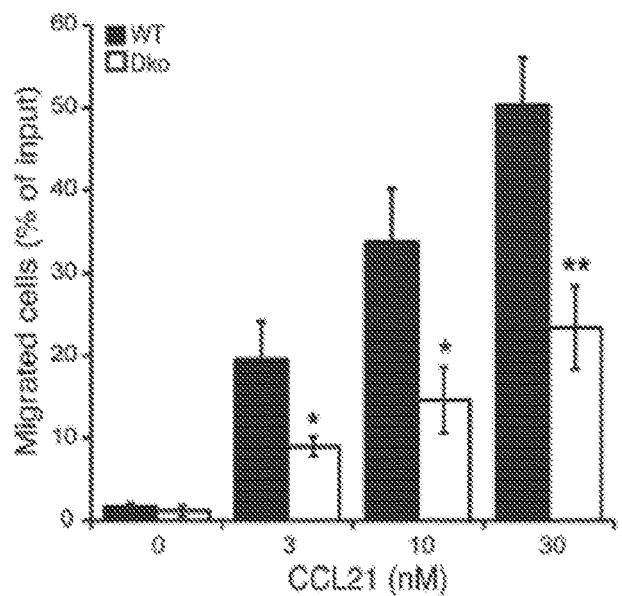
Figure 3B:
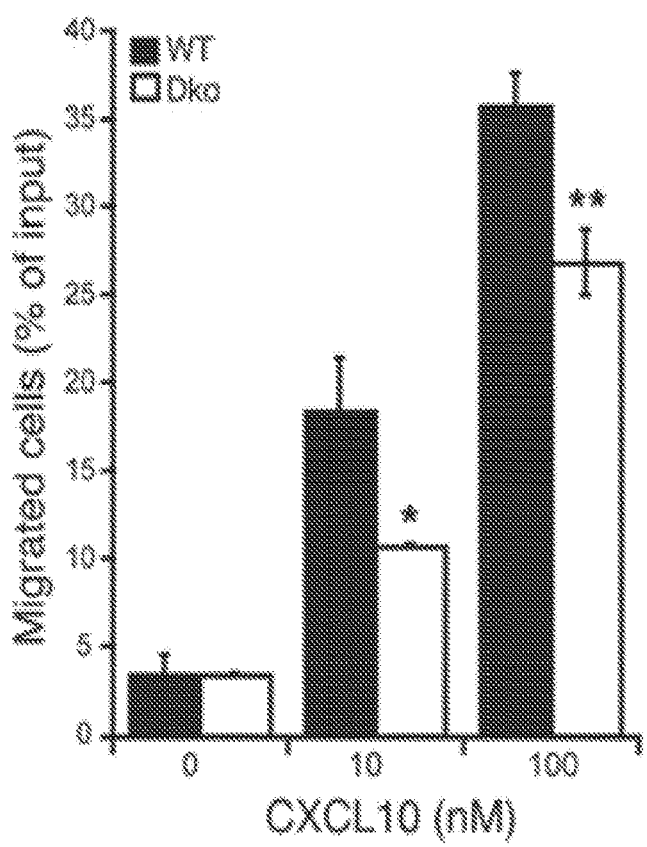
Figure 3C:
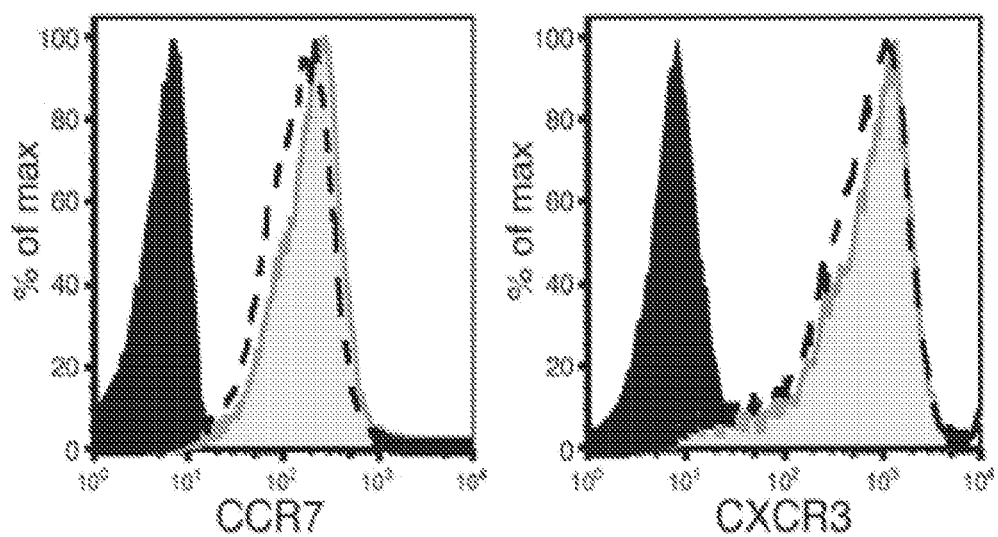
Figure 3D:
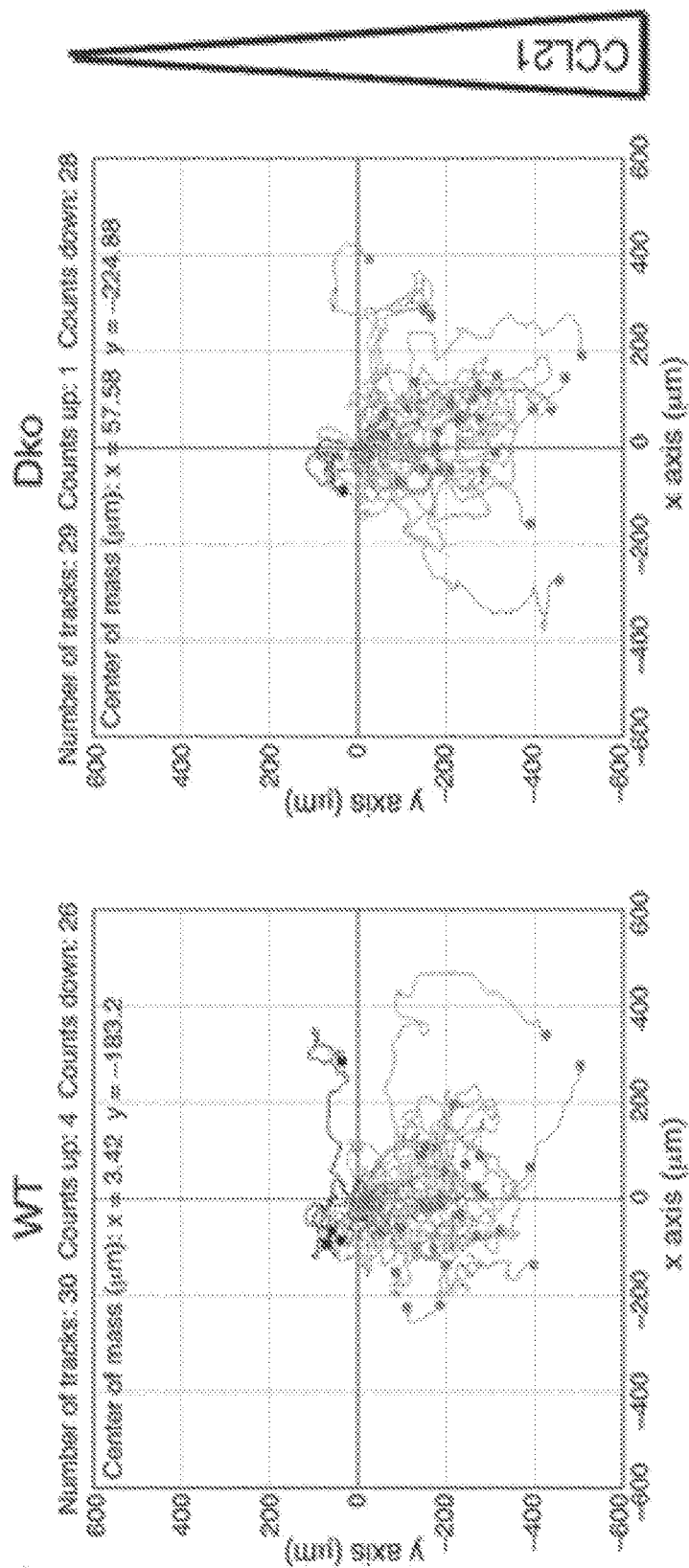

FIGS. 3A-3D show that CRK/CRKL-deficient T cells show defects in chemotaxis in settings where integrin function is required. Preactivated WT and CRK/CRKL Dko CD4+ T cells were prepared, and migration in response to CCL21 (FIG. 3A) or CXCL10 (FIG. 3B) was tested by using a 3-μm-pore-size Transwell® chamber. Average±SD values from quadruplicate wells from 1 experiment, representative of 5 separate experiments, are shown. *P<0.05, **P<0.01. Flow cytometric analysis of chemokine receptor expression is shown in FIG. 3C. Left: Preactivated WT and CRK/CRKL Dko CD4+ T cells were incubated with recombinant mouse CCL19-Fc, followed by labeling with anti-human Fcγ-biotin, then streptavidin-PE. Right: Preactivated WT and CRK/CRKL Dko CD4+ T cells were stained with anti-CXCR3-PE. Black shaded: isotype control; Gray shaded: WT; Dashed line: Dko. To test migration in a setting where integrin function is dispensable, preactivated WT or CRK/CRKL Dko CD4+ T cells were placed in a 5-μm-pore collagen gel in the presence of a CCL21 gradient, and cell migration was imaged for 4 hours at 37° C. (FIG. 3D). Tracks of individual cells are presented with the same point of origin. Data are representative of 3 experiments. Quantitative analysis of cell movements is shown in Table 1. Tracks in FIG. 3D are from experiment 1.

Figure 4A:
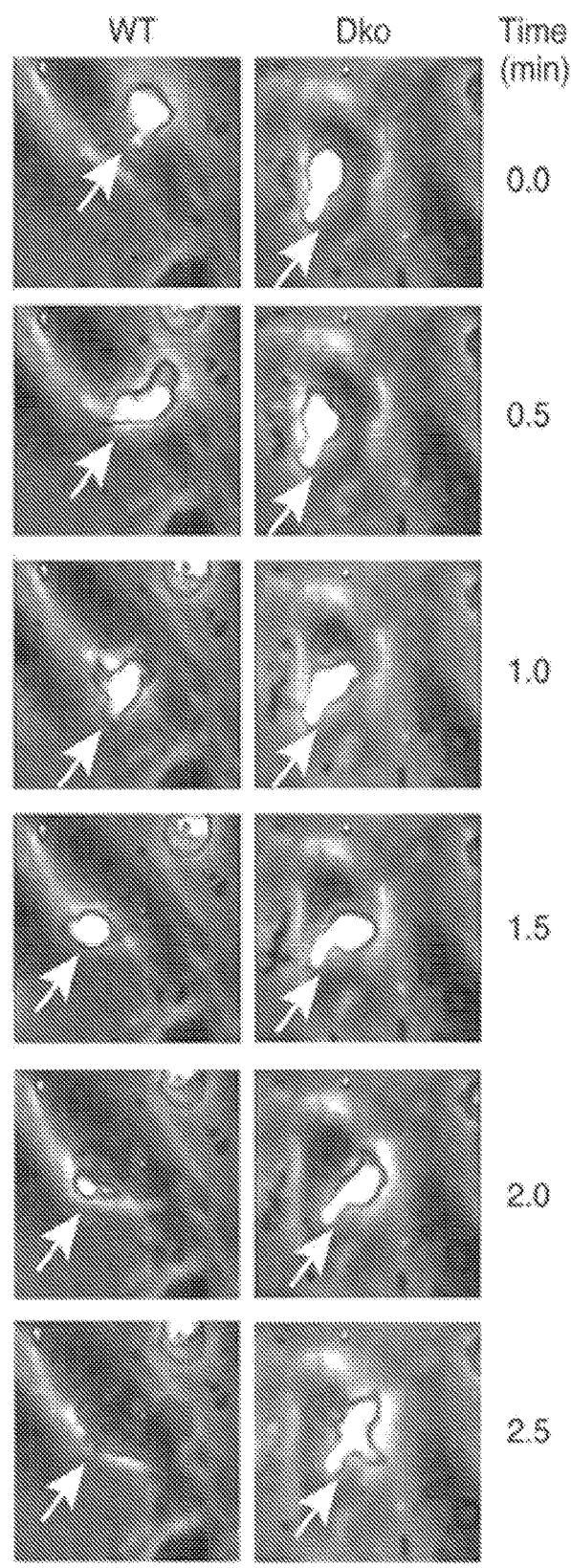
Figure 4B:
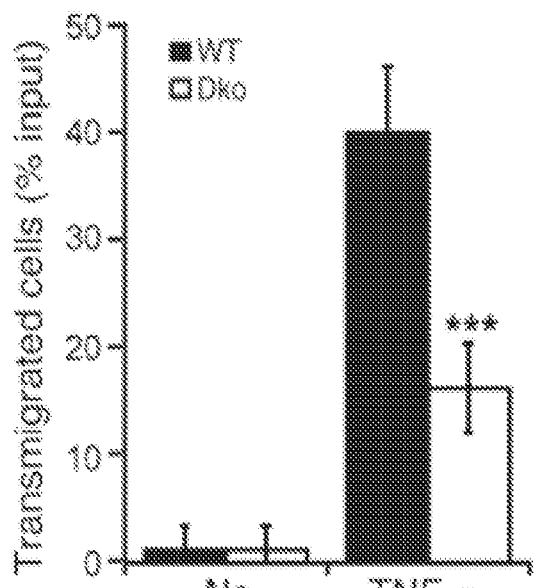
Figure 4C:
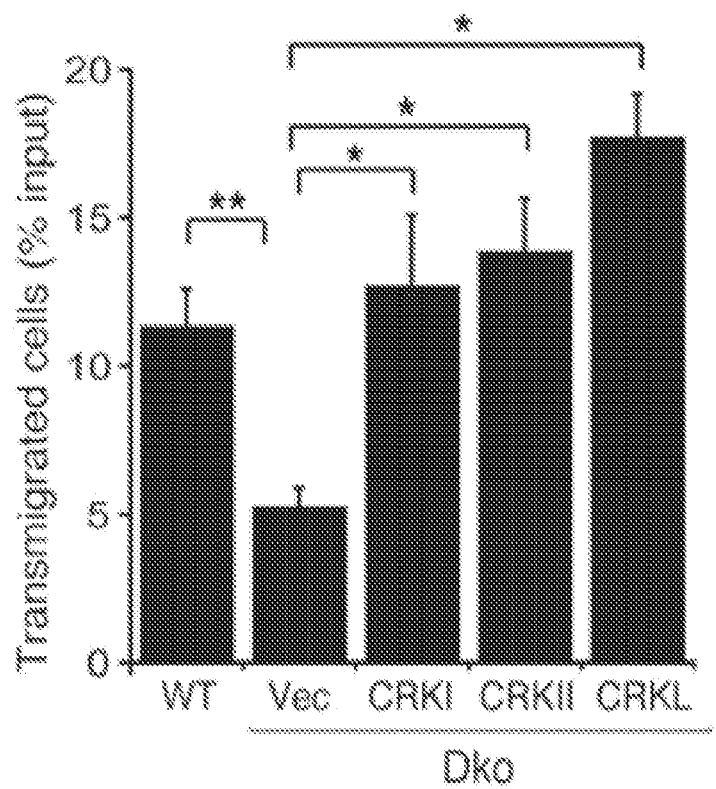
Figure 4D:
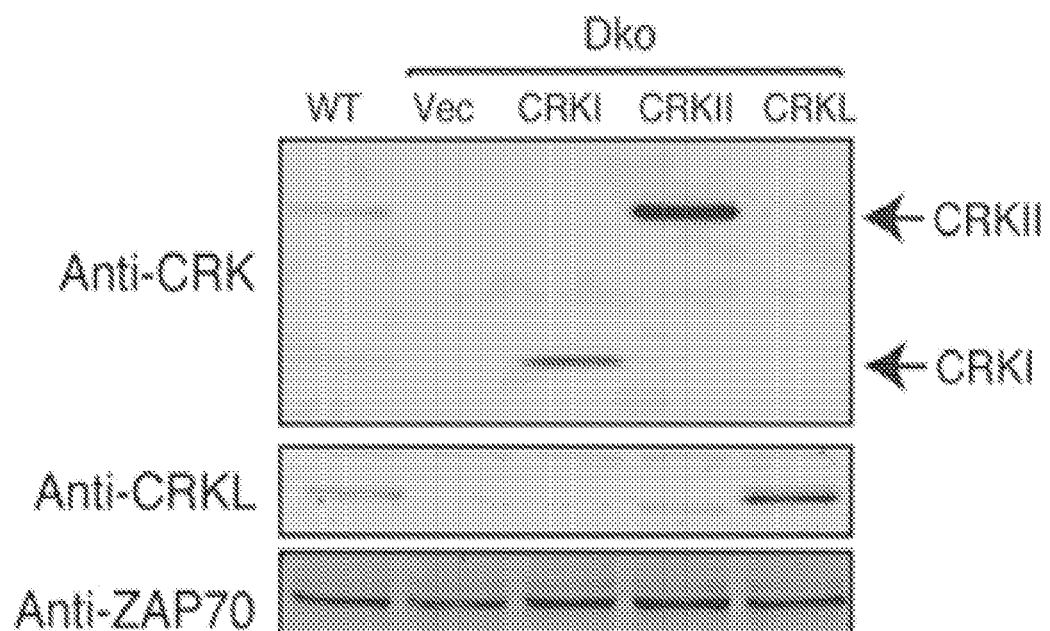
Figure 4E:
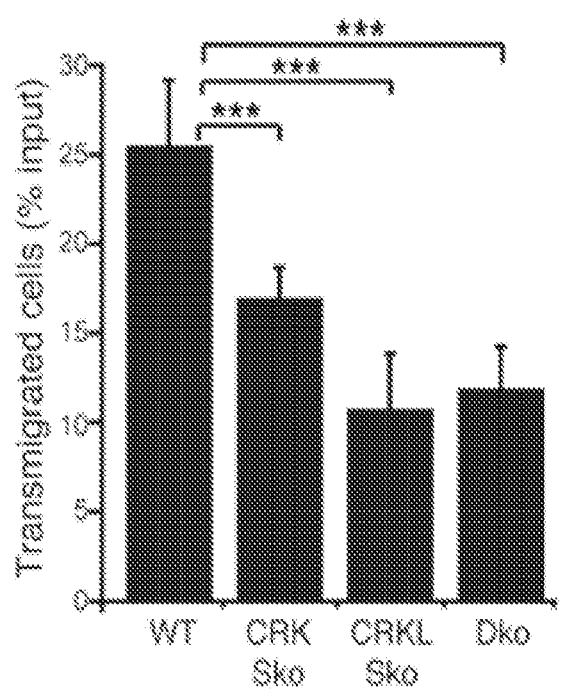

FIGS. 4A-4E show that CRK/CRKL-deficient T cells show defects in diapedesis and that CRK and CRKL show functional redundancy with CRKL being the more important isoform in this assay. 3B-11 endothelial cell monolayers were treated with TNF-α overnight, and preactivated WT or CRK/CRKL Dko CD4+ T cells were added on top. Images were collected every 30 seconds for 2 hours. Selected time-lapse images of WT T cells (left, arrows) and CRK/CRKL Dko T cells (right, arrows) acquired at the indicated time points are shown (FIG. 4A). T cells that transmigrated across the endothelial monolayer were scored, and average±SD values from 4 different experiments are shown. A total of 80 cells per genotype were scored (FIG. 4B). 3B-11 cells were grown as a monolayer on top of Transwellt inserts and treated with TNF-α. CRK/CRKL Dko CD4+ T cells were reconstituted with the indicated CRK isoforms and applied to the Transwell® inserts. T cells that underwent diapedesis were collected and analyzed by flow cytometry (FIG. 4C). Cells were then blotted with the indicated antibodies (FIG. 4D). Data represent mean±SD for triplicate samples from 1 experiment, representative of 4 independent experiments. Preactivated CD4+ T cells prepared from mice that were singly deficient (Sko) for either CRK or CRKL were applied to 3B-11 monolayers on Transwell® inserts, and T cell diapedesis was assessed (FIG. 4E). Data represent mean±SD from 3 independent experiments. *P<0.05. P<0.01, *P<0.005.

Figure 5A:
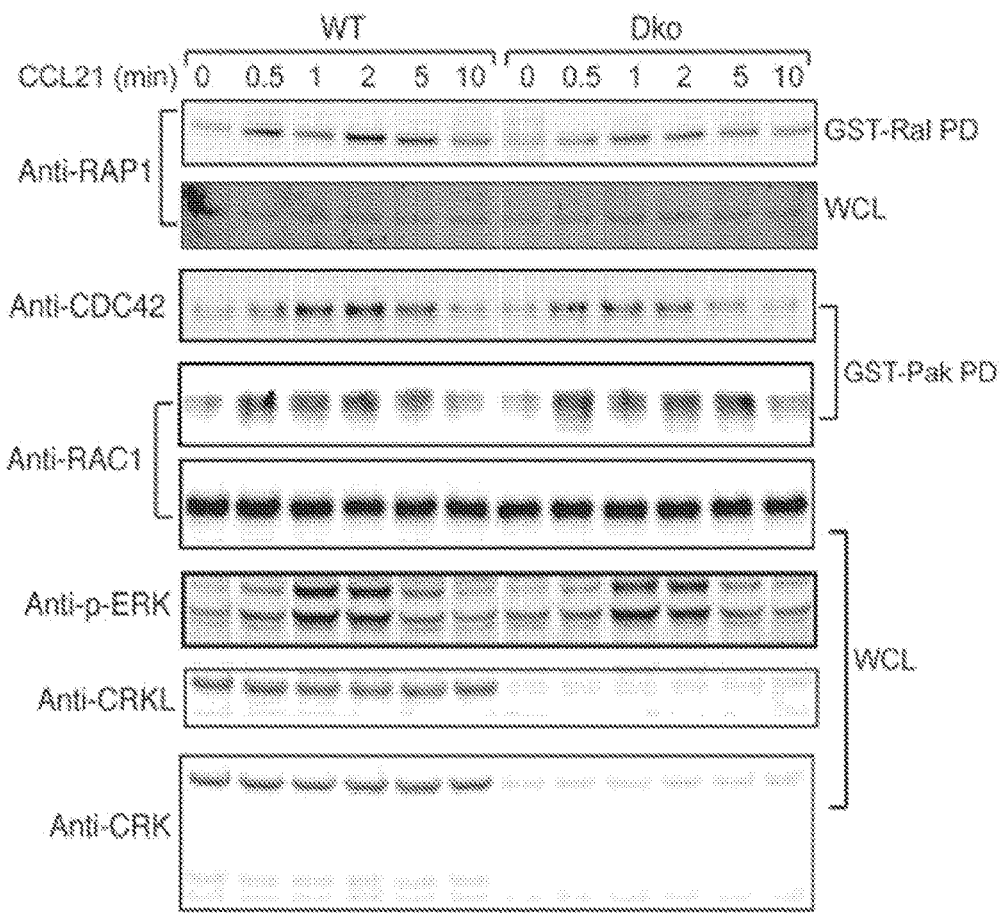
Figure 5B:
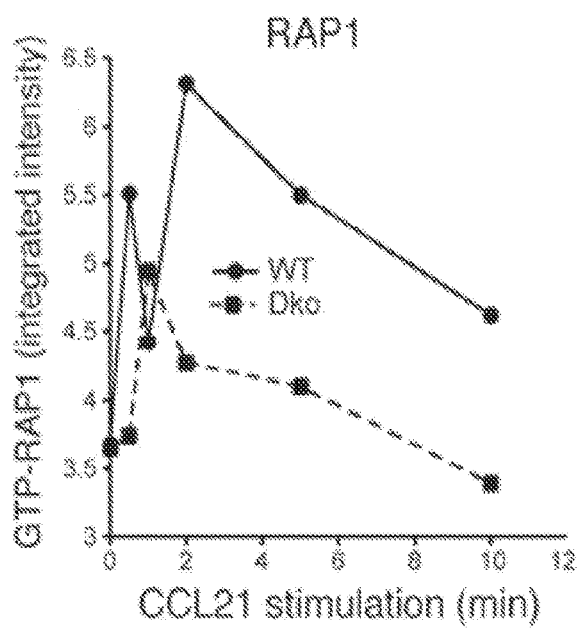
Figure 5C:
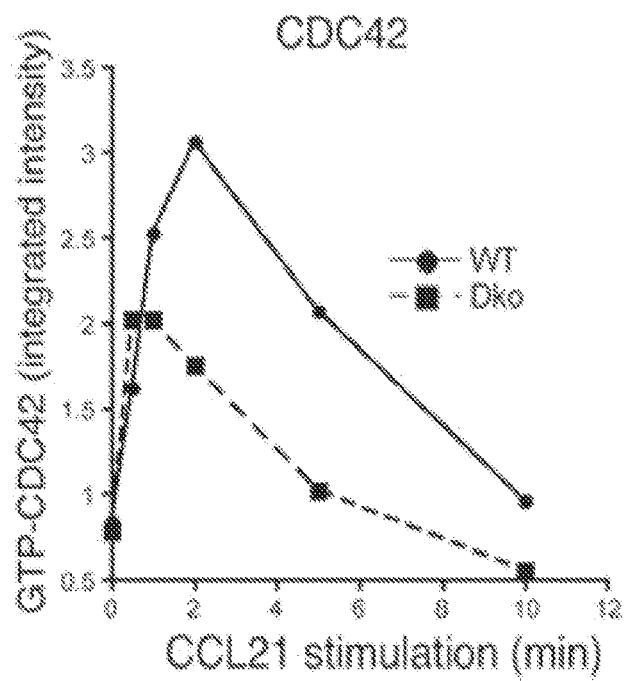
Figure 5D:
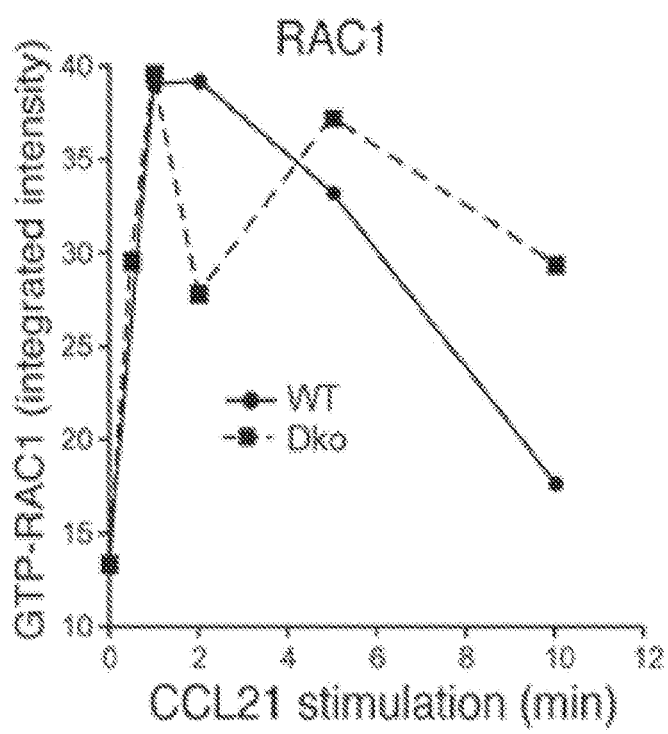
Figure 5E:
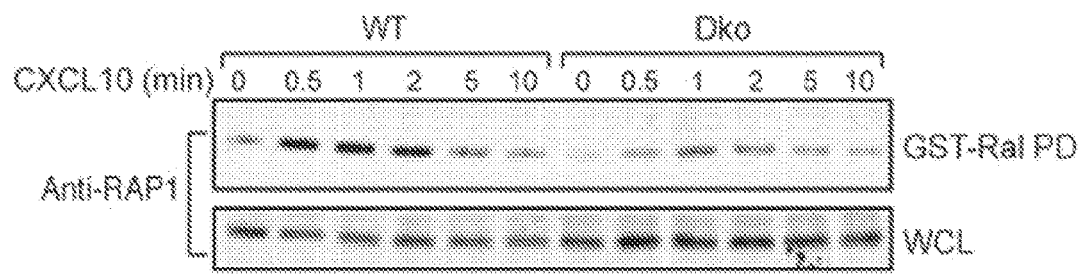
Figure 5F:
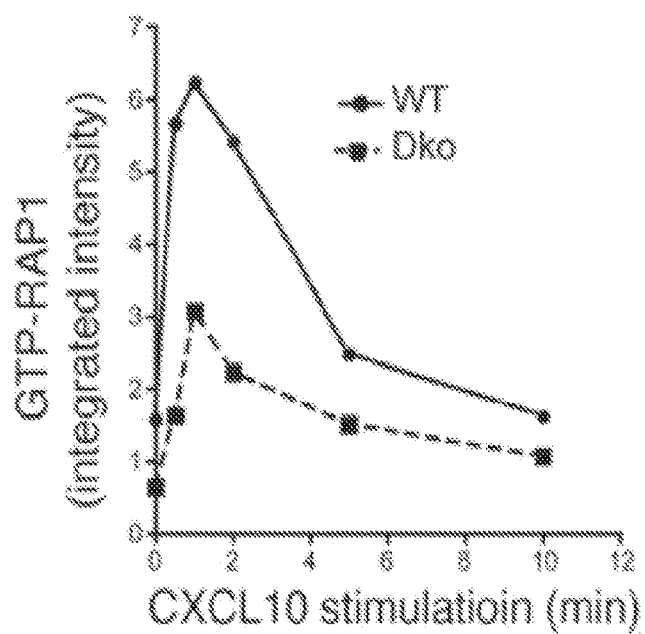

FIGS. 5A-SF show that RAC1 activation is intact, but RAP1 and CDC42 activation is defective in CRK/CRKL-deficient T cells. Preactivated WT and CRK/CRKL Dko CD4+ T cells were stimulated with 10 nM CCL21 for the indicated times. Whole cell lysates (WCL) were subjected to pull-down with GST-RalGDS (GST-Ral PD) or GST-PakRBD (GST-PAK PD). Bound proteins were analyzed by SDS-PAGE and immunoblotted with the indicated antibodies (FIG. 5A). Signals obtained for GTP-RAP1. GTP-CDC42, and GTP-RAC1 were quantified using a fluorescence-based detection system (FIGS. 5B-5D). WT and CRK/CRKL Dko CD4+ T cells were cultured under Th1-skewing conditions and stimulated with 10 nM CXCL10. Activation of RAP1 was assessed (FIG. 5E) and quantified (FIG. 5F). Representative data from at least 3 experiments are shown.

Figure 6A:
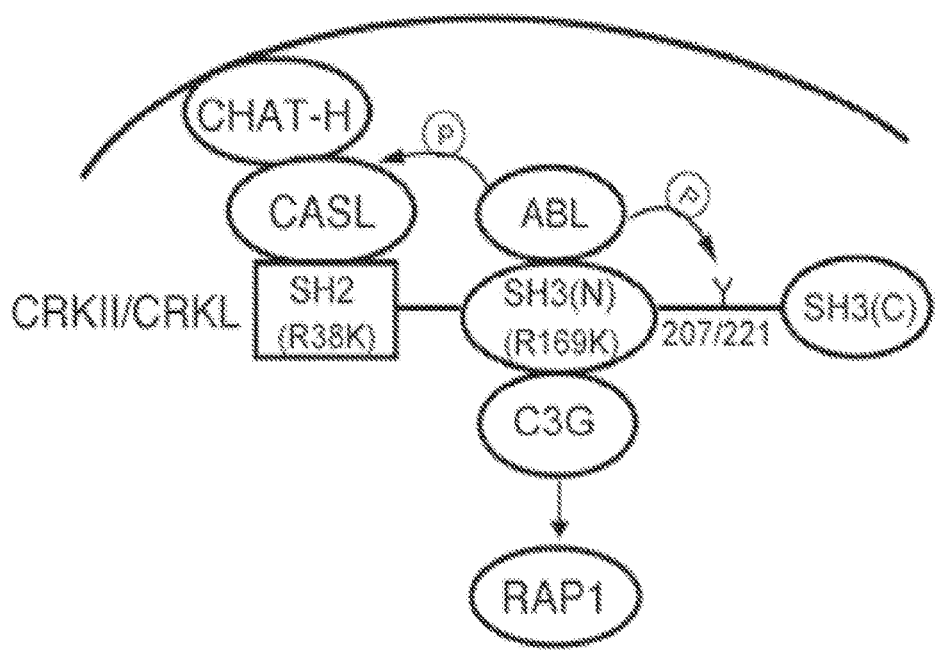
Figure 6B:
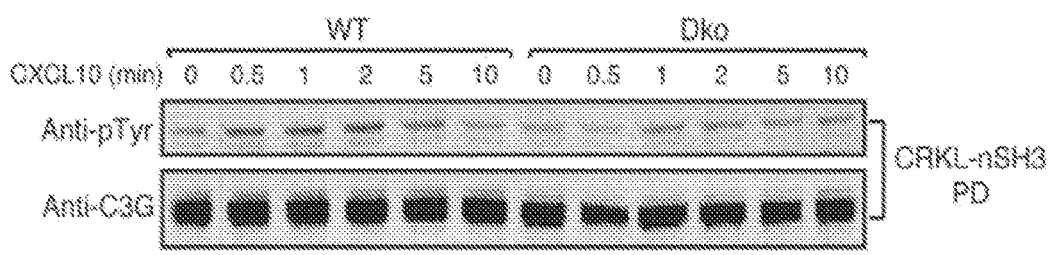
Figure 6C:
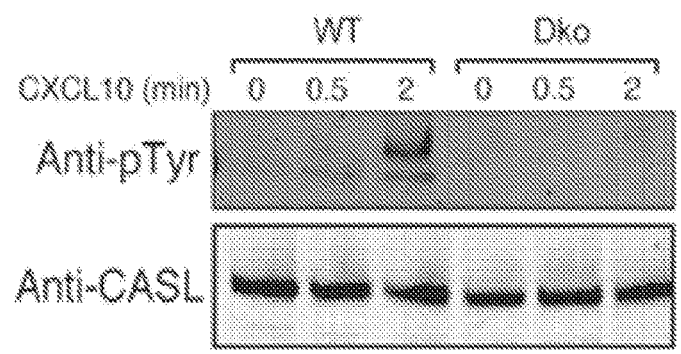
Figure 6D:
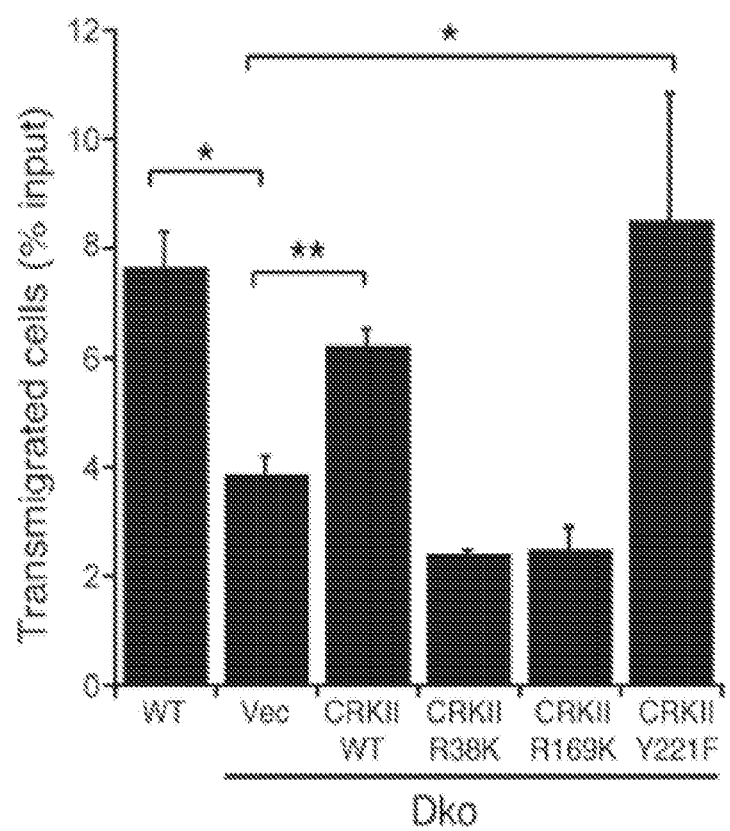

FIGS. 6A-6D show that CRK and CRKL interact with C3G and CASL to regulate T cell diapedesis. FIG. 6A provides a schematic drawing showing a proposed CHAT-H-CASL-CRK/CRKL-C3G module that could regulate RAP1 activation in response to chemokine stimulation. CASL binds to the SH2 domains of CRK proteins, and mutation of the SH2 domain (CRKII R38K) interrupts this association. Both C3G and c-ABL bind to the nSH3 domains of CRK and CRKL, and mutation in the SH3 domain (CRKII R169K) interrupts these interactions. c-ABL phosphorylates CASL, CRKII at Y221, and CRKL at Y207. CHAT-H constitutively associates with CASL and recruits CASL to the plasma membrane. Chemokine stimulation induces CASL tyrosine phosphorylation by ABL family kinases and provides binding sites for the SH2 domains of CRK proteins. The association between CRK and CASL brings C3G to the membrane and activates RAP1. Preactivated CD4+ T cells were stimulated with CXCL10 for the indicated times, lysed, and incubated with recombinant CRKL-SH3 protein to pull down C3G or immunoprecipitated with anti-CASL. The precipitants were blotted with the indicated antibodies (FIGS. 6B and 6C). CRK/CRKL Dko CD4+ T cells were reconstituted with the indicated CRKII mutants, and diapedesis was assessed (FIG. 6D). Data represent mean±SD of replicate samples from 1 experiment, representative of 4 independent experiments. *P<0.05, **P<0.01.

Figure 7A:
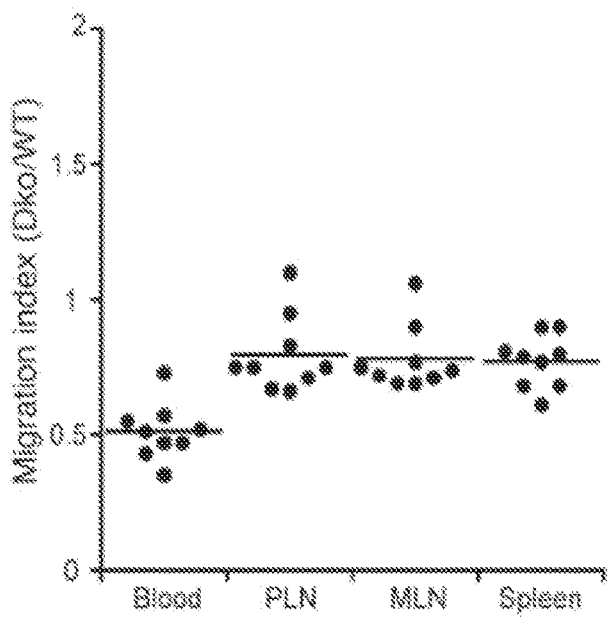
Figure 7B:
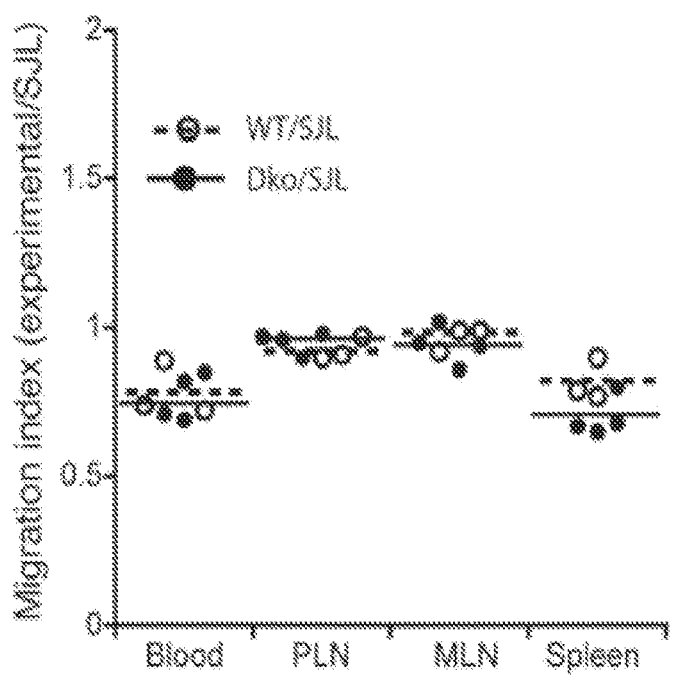
Figure 7C:
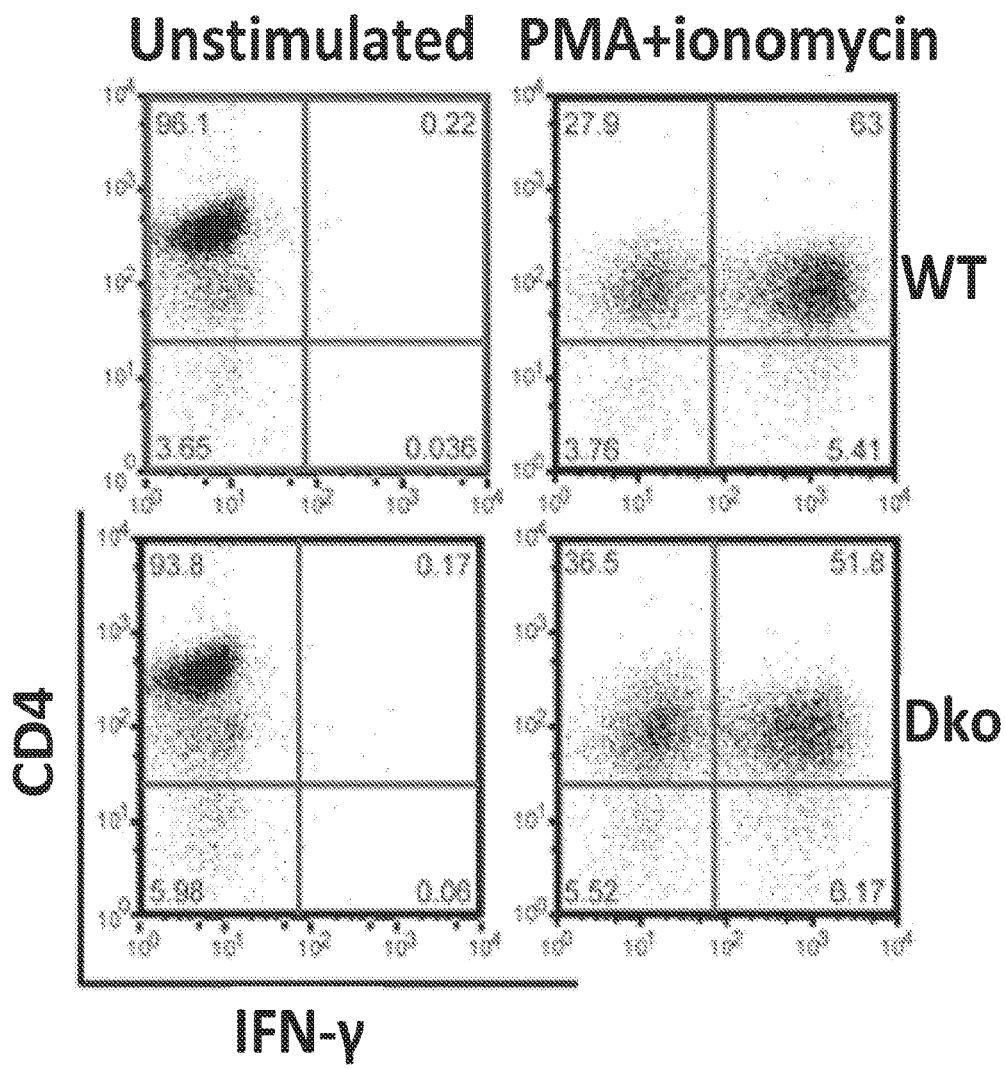
Figure 7D:
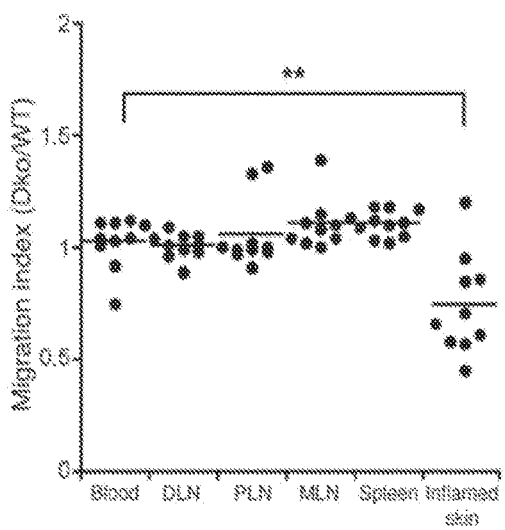

FIGS. 7A-7D show that CRK/CRKL-deficient T cells have defects in migration to inflamed skin but not in homing to lymphoid organs. Resting WT or Dko CD4+T lymphoblasts were labeled with CFSE or CMTMR, mixed, and injected into recipient mice. One hour after injection, cells were collected from blood, peripheral lymph nodes (PLN), mesenteric lymph nodes (MLN), and spleen, and the ratio of Dko to WT T cells was determined (FIG. 7A). Pooled data from 3 experiments is shown (n=9 total mice). To analyze naïve T cell homing, PLN lymphocytes from WT mice (CD45.2+) were labeled with CFSE, mixed with PLN lymphocytes from B6.SJL mice (CD45.1+), and injected i.v. into recipient mice. In parallel, PLN lymphocytes from CRK CRKL Dko Rosa-YFP mice (CD45.2+) were mixed with PLN lymphocytes from B6.SJL mice (CD45.1+) and injected into recipient mice (CD45.2+). Cells were harvested from blood, PLN, MLN, and spleen 1 hour after transfer, and the ratio of naive (CD62Lhi, CD44lo) experimental (CFSE+ WT or EYFP+Dko) to competitor (CD45.1+) CD4+ T cells in the recovered populations was determined and normalized to the input ratio (FIG. 7B). Data represent individual mice from 1 experiment (n=7 total mice). To assess T cell migration to inflamed skin, CD4+ T cells were purified from WT and Dko mice, and Th1 cells were cultured in vitro. Percentages of WT and Dko Th1 cells were analyzed by intracellular flow. Skin inflammation was induced in recipient mice using DNFB. WT and Dko Th1 cells were stained with CFSE or CMTMR, mixed 1:1, and injected intravenously into recipient mice. Twenty-four hours after injection, blood, draining lymph nodes (DLN), PLN, MLN, spleen, control skin, and inflamed skin were collected, and adoptively transferred cells were analyzed by flow cytometry (FIG. 7D). Combined data from 3 experiments (n=10 total mice) are shown. **P<0.01.

Figure 8A:
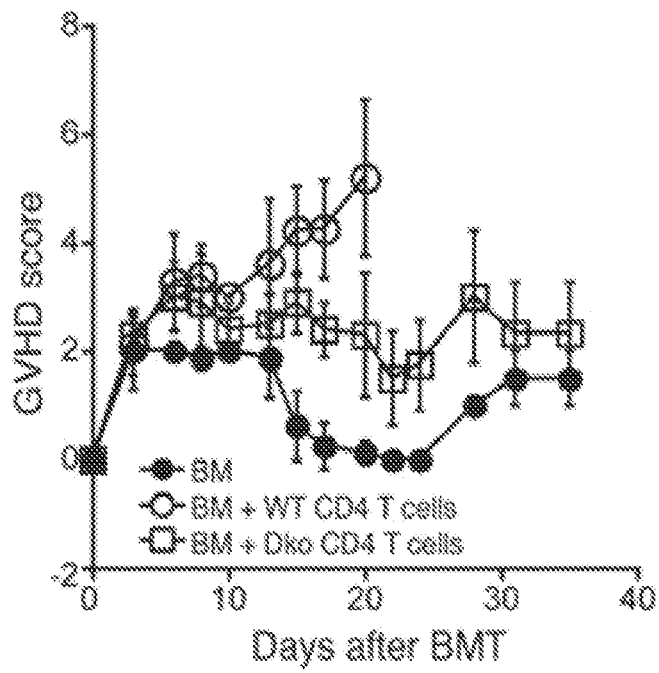
Figure 8B:
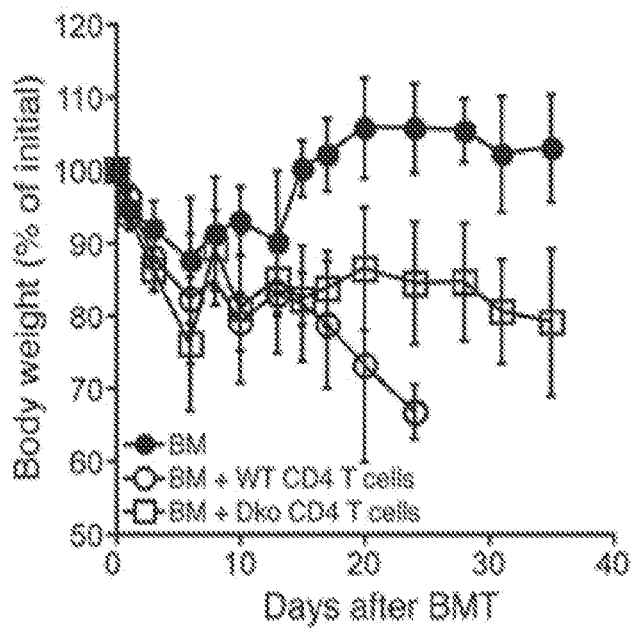
Figure 8C:
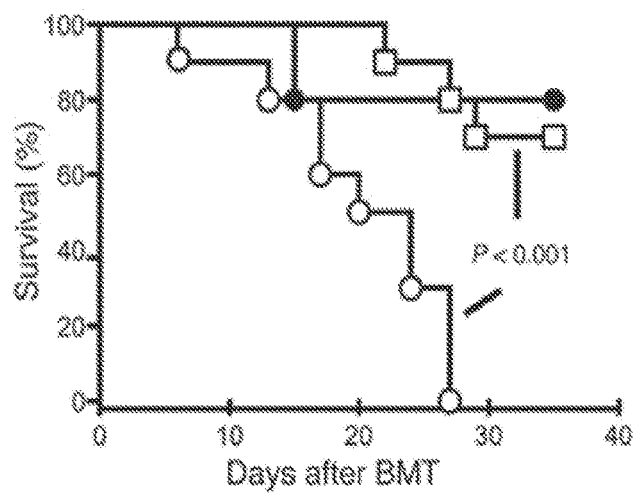
Figure 8D:
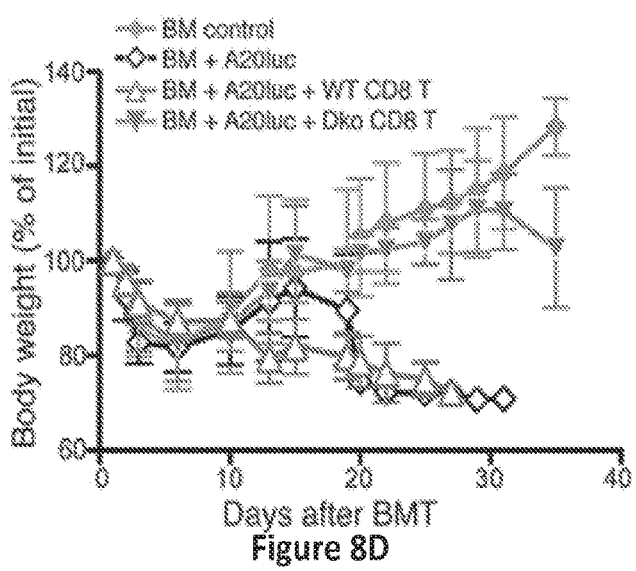
Figure 8E:
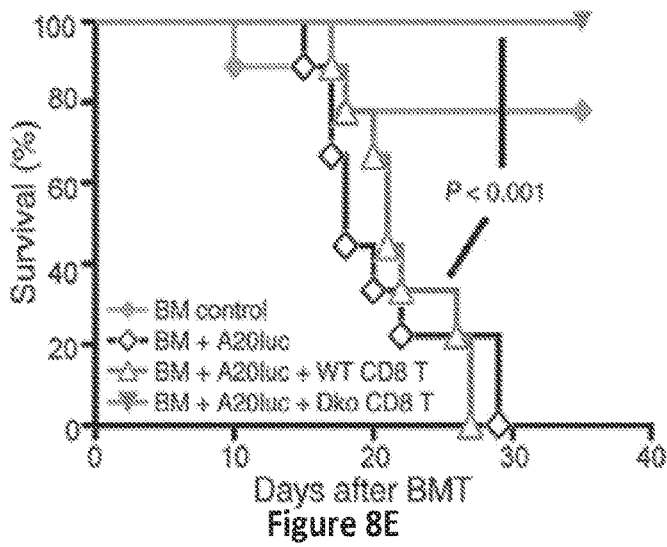
Figure 8F:
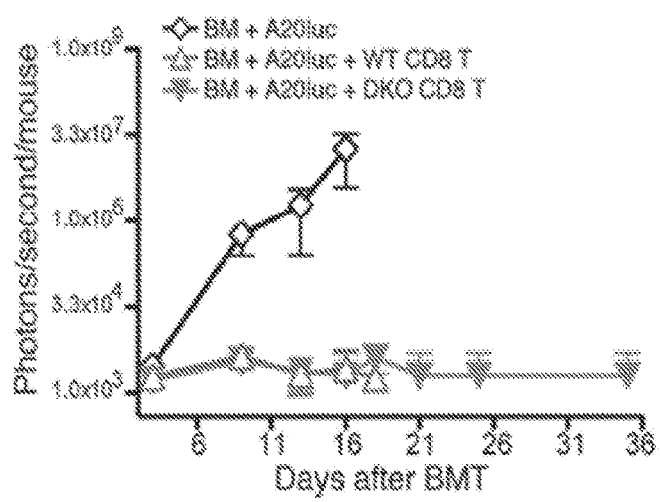
Figure 8G:
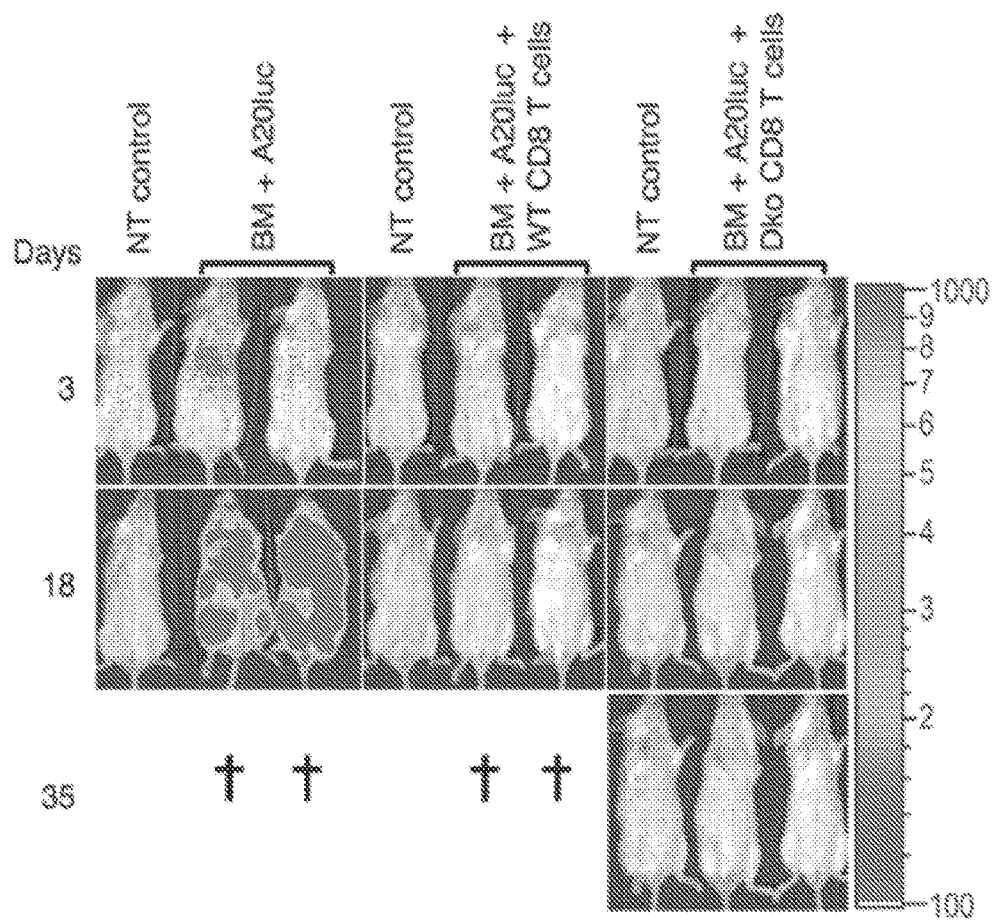
Figure 8H:
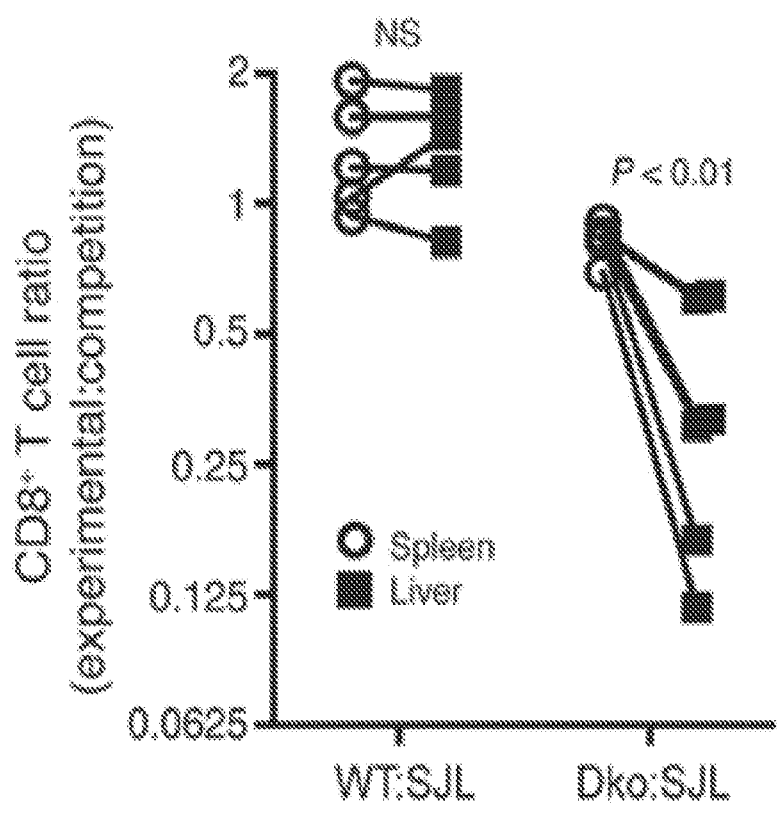

FIGS. 8A-8H show that CRK/CRKL Dko donor T cells can carry out GVL with minimal GVHD. T cell-depleted bone marrow cells alone (BM, H-2b), mixed with purified WT CD4$^+$ T cells (BM+WT CD4 T cells, H-2b), or mixed with purified CRK/CRKL Dko CD4+ T cells (BM+Dko CD4 T cells, H-2b) were injected into lethally irradiated BALB/c hosts (H-2d). Host GVHD clinical scores (FIG. 8A), body weight change (FIG. 8B), and survival (FIG. 8C) are summarized. Combined data from 2 different experiments are shown, with a total of 5-10 mice for each experimental group. Lethally irradiated BALB/c hosts were injected with T cell-depleted bone marrow cells alone (BM control), or together with luciferase-transduced A20 cells (BM+A20luc), purified WT CD8+ T cells (BM+A20luc+ WT CD8 T), or CRK/CRKL Dko CD8+ T cells (BM+ A20luc+Dko CD8 T). Host body weight change (FIG. 8D), survival (FIG. 8E), and tumor burden (reflected by the luciferase signal) (FIGS. 8F and 8G) are summarized. FIG. 8E shows combined data from 2 different experiments, with a total of 8-10 mice per experimental group. FIGS. 8D and 8F show data from 1 of 2 independent experiments, with 5 mice for each experimental group. To assess T cell migration during GVHD, congenically marked CD8+ T cells from WT or CRK/CRKL Dko mice were mixed 1:1 with competitor SJL T cells (all H-2b) and injected together with T cell-depleted bone marrow cells into lethally irradiated BALB/c host mice (H-2d). Spleen and liver were harvested after 10-12 days, and the ratio of experimental (WT or Dko) to competitor adoptively transferred cells was determined (FIG. 8H). Paired data (combined from 2 experiments) are shown, with a total of 5 (WT) or 6 (Dko) recipient mice. Error bars represent mean±SD.

Figure 9A:
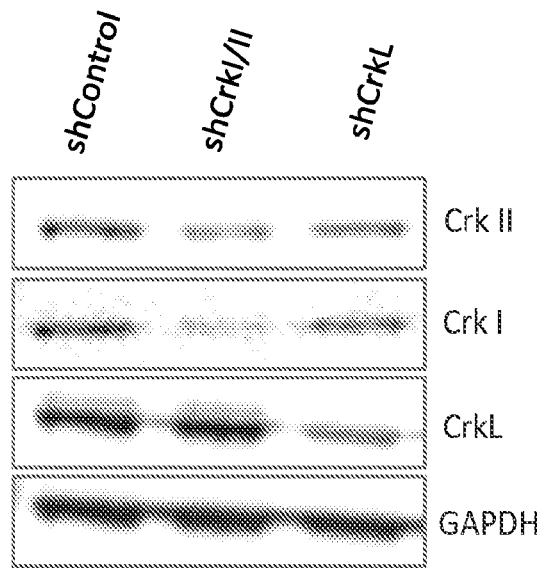
Figure 9B:
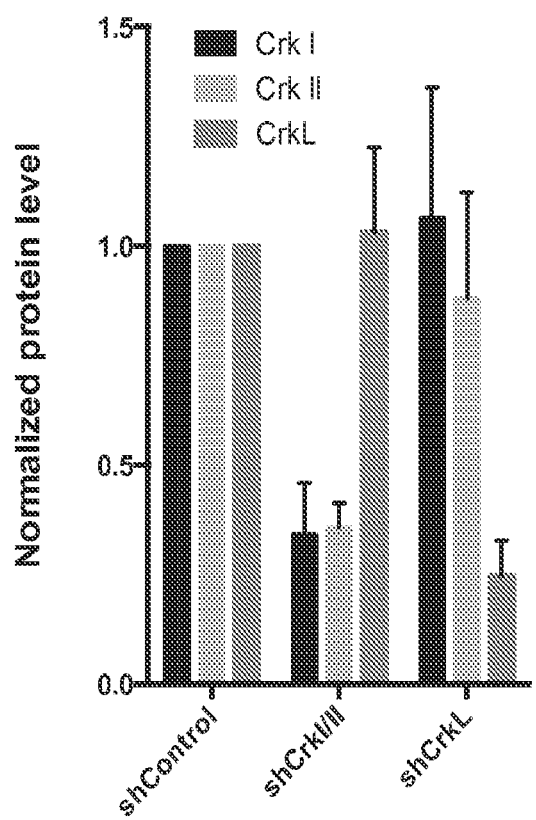

FIG. 9A is an image of a Western blot showing the expression of CrkI, CrkII, and CrkL in activated human CD4 cells treated with a control short hairpin (sh) RNA (shControl), a CrkI/II shRNA (shCrkI/II), or a CrkL shRNA (shCrkL). FIG. 9B provides a quantitative analysis of the data in FIG. 9A, measured using a fluorescence-based imaging system. Combined data from 5 experiments are shown. In each case, levels were normalized to the shControl. Error bars represent mean+/−SD. P<0.0001 for each protein, compared with their respective shControl.

Figure 10A:
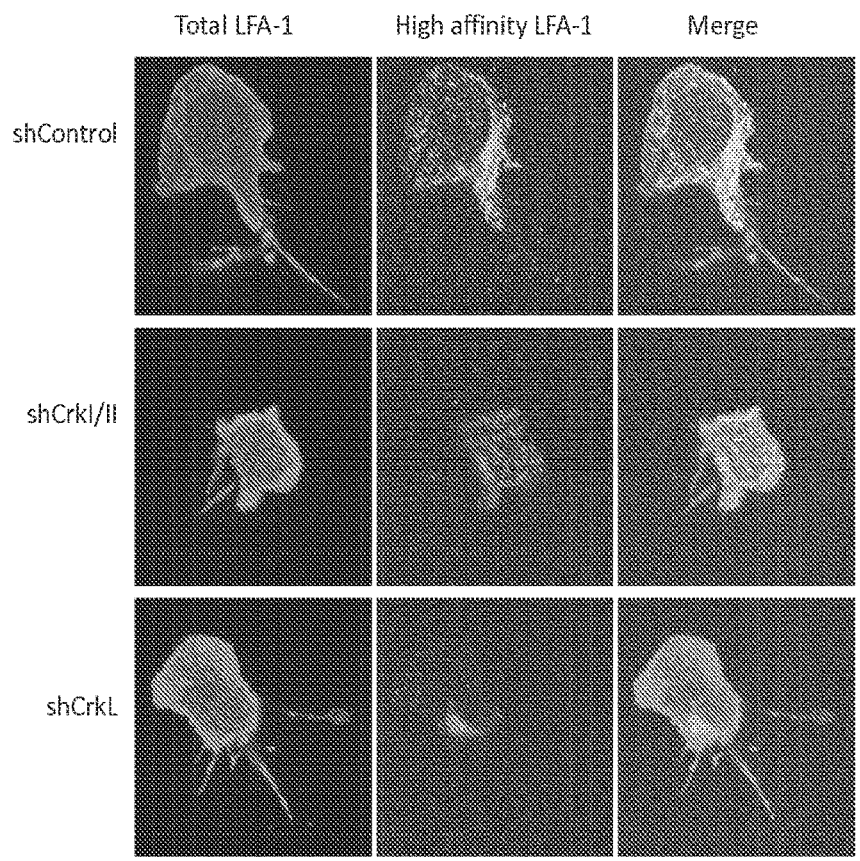
Figure 10B:
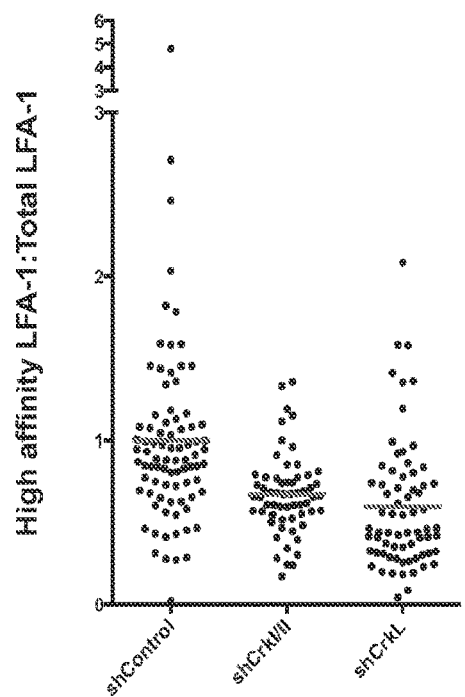

FIG. 10A shows that suppression of CRKI/II or CRKL leads to loss of integrin conversion to the high affinity confirmation. Images show activated human peripheral blood CD4$^+$ T cells treated with a control shRNA (shControl), a CrkI/II shRNA (shCrkI/II), or a CrkL shRNA (shCrkL). T cells were plated on ICAM-1+SDF-1 to induce spreading and allow integrin activation and engagement. Cells were then surface stained for total lymphocyte function-associated antigen 1 (LFA-1) (using monoclonal antibody TS2/4) and the extended open high affinity confirmation of LFA-1 (using monoclonal antibody m24). FIG. 10B provides a quantitative analysis of the data in FIG. 10A. Each dot represents one call. Bars represent means. P<0.001 for both shCRKI/II and shCRKL, as compared with shControl.

Figure 11:
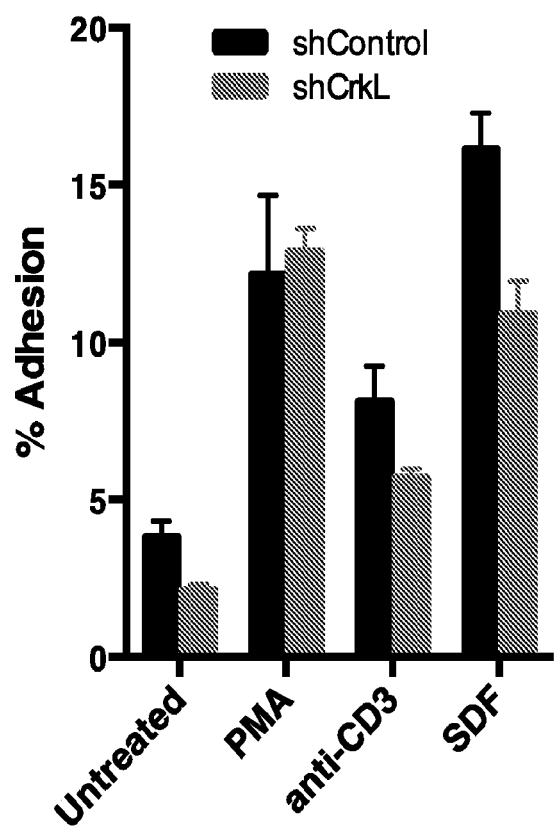

FIG. 11 shows that suppression of CRKL leads to diminished binding of activated human peripheral blood CD4$^+$ T cells to integrin ligands. Cells were treated with a control shRNA (shControl) or a CrkL shRNA (shCrkL), and allowed to interact with plates coated with ICAM-1 in the presence of the indicated stimuli. The proportion of input cells that bound to the plates was quantified. Data represent means+/− SD from replicate wells in a single experiment, representative of at least three experiments. Untreated, P<0.01; PMA, n.s.; anti-CD3, P<0.05; SDF, P<0.005.

DETAILED DESCRIPTION OF THE INVENTION

Effector T cell migration into inflamed sites greatly exacerbates tissue destruction and disease severity in inflammatory diseases, including graft-versus-host disease (GVHD). T cell migration into such sites depends heavily on regulated adhesion and migration, but the signaling pathways that coordinate these functions downstream of chemokine receptors are largely unknown. Using conditional knockout mice, it is shown herein that T cells lacking the adaptor proteins CRK and CRK-like (CRKL) exhibit reduced integrin-dependent adhesion, chemotaxis, and diapedesis. Moreover, these two closely related proteins exhibited substantial functional redundancy, as ectopic expression of either protein rescued defects in T cells lacking both CRK and CRKL. It is determined that CRK proteins coordinate with the RAP guanine nucleotide exchange factor C3G and the adhesion docking molecule CASL to activate the integrin regulatory GTPase RAP1. CRK proteins were required for effector T cell trafficking into sites of inflammation, but not for migration to lymphoid organs. In a murine bone marrow transplantation model, the differential migration of CRK/CRKL-deficient T cells resulted in efficient graft-versus-leukemia responses with minimal GVHD. Together, the results provided herein show that CRK family proteins selectively regulate T cell adhesion and migration at effector sites and indicate that these proteins are therapeutic targets for preventing GVHD.

CRK proteins are key regulators of adhesion and migration in many cell types. This family of ubiquitously expressed adaptors consists of CRKI, CRKII (products of the CRK gene), and CRK-like (CRKL), encoded by an independent gene, CRKL. CRKII and CRKL contain one SH2 domain followed by two SH3 domains (designated nSH3 and cSH3), whereas the splice variant CRKI lacks the cSH3 domain. The nSH3 domain of CRK proteins binds to C3G and DOCK180, which are guanine-nucleotide exchange factors (GEFs) for the small GTPases RAP1 and RAC1, respectively (Birge et al. (2009) Cell Commun. Signal., 7:13). RAP1 controls adhesion, while RAC1 controls actin polymerization. Binding of the SH2 domain of CRK proteins with p130Cas/CASL/EFS family proteins is important for localization of CRK to the plasma membrane (Birge et al. (2009) Cell Commun. Signal., 7:13; Klemke et al. (1998) J. Cell. Biol., 140:961-972). In contrast to the nSH3 and SH2 domains, the cSH3 domain of CRKII engages in intramolecular interactions that negatively regulate CRKII function by stabilizing a closed, autoinhibited state (Kobashigawa et al. (2007) Nat. Struct. Mol. Biol., 14:503-510). In addition, CRKII and CRKL have a regulatory tyrosine (Y221 in CRKII, Y207 in CRKL) that is phosphorylated by ABL family kinases (Feller et al. (1994) EMBO J., 13:2341-2351; de Jong et al. (1997) Oncogene 14:507-513). Phosphorylation of CRKII at Y221 creates a binding site for the SH2 domain, and the resulting intramolecular interaction blocks accessibility of the SH2 and nSH3 domains to other binding partners and terminates CRKII signaling (Feller et al. (1994) EMBO J., 13:2341-2351). CRKI, which lacks the regulatory cSH3 domain and phosphorylation site, exhibits constitutively active adaptor function (Birge et al. (2009) Cell Commun. Signal., 7:13; Matsuda et al. (1992) Mol. Cell Biol., 12:3482-3489).

Despite their importance in other cell types, the function of CRK proteins in T cells is poorly understood. Progress in this area has been hindered by the existence of profound developmental abnormalities in mice with germline deletion of CRK proteins—the majority of Crk-null and Crkl-null mice die during embryonic development (Guris et al. (2001) Nat. Genet., 27:293-298; Park et al. (2006) Mol. Cell Biol., 26:6272-6782)—and by problems posed by functional redundancy. The few studies that have been performed have focused on the T cell receptor (TCR) signaling pathway, and results are conflicting. Using the small number of surviving $Crkl^{-/-}$ mice, it has been shown that thymocyte number was reduced, but T cell differentiation and activation were intact (Peterson et al. (2003) Eur. J. Immunol., 33:2687-2695). In contrast, others have used RNAi to suppress CRKL expression in Jurkat cells and ex vivo human T cells and defects in integrin activation and cytokine production downstream of TCR engagement were observed (Nolz et al. (2008) J. Cell Biol., 182:1231-1244). Neither study addressed chemokine-dependent T cell responses. Further, neither study addressed possible functional redundancy between CRKL and the closely related proteins CRKI and CRKII.

To circumvent developmental problems and allow analysis of T cells lacking all CRK proteins, mice bearing floxed alleles of both Crk and Crkl were used. These mice have been used successfully to delete Crk and Crkl in neuronal progenitor cells, resulting in defects in the Reelin signaling pathway and failure of neuronal migration (Park et al. (2008) J. Neurosci., 28:13551-13562). It is shown herein that conditional deletion of Crk and Crkl genes late in T cell development leads to impaired activation of RAP1 and defective adhesion, chemotaxis, and diapedesis. Interestingly, it was found that CRK/CRKL-deficient T cells show selective trafficking defects in vivo; these cells homed efficiently to lymphoid organs but migrated poorly to sites of inflammation. The differential migratory activity of CRK/CRKL-deficient T cells has important therapeutic implications, since they can carry out graft-versus-leukemia (GVL) responses with minimal GVHD.

As stated above, the role for CRK proteins in regulating chemokine-dependent adhesion, migration, and diapedesis of T cells is shown herein. These molecules are placed in the signaling pathway linking chemokine receptor engagement to integrin activation. Surprisingly, it was found that T cells lacking CRK proteins maintain effector function and the ability to home to lymphoid organs, but show selective defects in migration into inflamed tissues. This phenotype has important therapeutic implications, since T cells lacking CRK proteins can carry out effective GVL responses while eliciting minimal GVHD-associated morbidity and mortality.

At the molecular level, it is shown that CRK proteins function to promote chemokine-dependent integrin activation by RAP1, a key event needed for adhesion to endothelial cells and subsequent diapedesis (Shimonaka et al. (2003) J. Cell Biol., 161:417-427). CRK proteins signal through the RAP1GEF C3G to regulate RAP1 activation (Birge et al. (2009) Cell. Commun. Signal 7:13; Nolz et al. (2008) J. Cell Biol., 182:1231-1244: Park et al. (2008) J. Neurosci., 28:13551-13562; Zhang et al. (2003) J. Biol. Chem., 278: 23978-23983). Herein, it is shown that this pathway is important for chemokine-induced T cell adhesion and migration. In other systems, CRK-dependent activation of C3G involves both recruitment of C3G to the cell membrane and phosphorylation at Tyr504 (Ichiba et al. (1997) J. Biol. Chem., 272:22215-22220; Ichiba et al. (1999) J. Biol. Chem., 274:14376-14381). Consistent with this, chemokine-stimulated C3G phosphorylation was reduced in CRK protein-deficient T cells. It was observed that in addition to playing a role in inside-out signaling pathways leading to integrin activation, CRK/CRKL Dko T cells polarized poorly in response to fibronectin ligation. This indicates that these proteins, like RAP1 (Shimonaka et al. (2003) J. Cell Biol., 161:417-427: Gérard et al. (2007) J. Cell Biol., 176:863-875), are also required for outside-in integrin signaling.

The work presented herein also sheds new light on the relevant upstream signaling events. CHAT-H (CAS and HEF-1-associated signal transducer in hematopoietic cells) constitutively binds to CASL (Sakakibara et al. (2000) J. Biol. Chem., 275:6404-6410), localizing the complex to the plasma membrane. Chemokine stimulation triggers CASL phosphorylation and recruits an unknown signaling intermediate to CHAT-H-CASL modules, leading to RAP1 activation (Regelmann et al. (2006) Immunity 25:907-918). Since CASL binds the SH2 domains of CRK proteins (Kanda et al. (1997) Eur. J. Immunol., 27:2113-2117), and mediates their localization to the plasma membrane (Klemke et al. (1998) J. Cell Biol., 140:961-972; Li et al. (2003) Mol. Cell Biol., 23:2883-2892), CRK proteins might be the missing intermediate in this complex. In support of this idea, it is shown herein that interaction of CASL and C3G with CRKII is required for CRK's function in regulating T cell diapedesis. Thus, a unified model can be proposed through which a CHAT-H-CASL-CRK/CRKL-C3G complex controls local RAP1 activation in migrating T cells (FIG. 6A).

In addition to regulating RAP1, CRK proteins can activate RAC1 by signaling through DOCK180 (Birge et al. (2009) Cell. Commun. Signal., 7:13). Surprisingly, however, it was found that RAC1 activation was intact in CRK/CRKL Dko T cells. Peripheral blood leukocytes express DOCK2 rather than DOCK180 (Nishihara et al. (1999) Biochim. Biophys. Acta 1452:179-187), and the connection between DOCK2 and CRK proteins is debated (Nishihara et al. (1999) Biochim. Biophys. Acta 1452:179-187; Nishihara et al. (2002) Blood 100:3968-3974). In support of the view that CRK proteins do not signal through DOCK2 in this system, the phenotypes of DOCK2 and CRK/CRKL-deficient T cells are very different. In $Dock2^{-/-}$ T cells, chemokine-induced RAC1 activation and actin polymerization are almost entirely abolished (Fukui et al. (2001) Nature 412:826-831), while adhesion and transendothelial migration are fairly normal (Nombela-Arrieta et al. (2004) Immunity 21:429-441; Shulman et al. (2006) Blood 108:2150-2158). In contrast, CRK/CRKL-deficient T cells were found herein to exhibit clear defects in adhesion and diapedesis, with more modest defects in migration. Indeed, migration in a 3D environment, a process that depends on RAC1-driven actin polymerization but not on integrins (Lämmermann et al. (2008) Nature 453:51-55), was normal. Although RAC1 activation was intact, activation of CDC42 was reduced in CRK/CRKL Dko T cells. This is an important finding, since CDC42 activity promotes T cell crawling along endothelial cells and probing for suitable sites for transendothelial migration (Shulman et al. (2009) Immunity 30:384-396). Evidently, the residual levels of CDC42 activation are sufficient to support directional T cell migration in the 3D collagen gel assay. Nonetheless, defects in CDC42 activity likely contribute to the diapedesis defects. Notably. CDC42 may be activated downstream of RAP (Gerard et al. (2007) J. Cell. Biol., 176:863-875) or other DOCK family proteins may be involved.

Phenotypically, there are similarities and differences between CRK-deficient and ABL-deficient T cells. T cells lacking c-ABL show chemotactic defects in Transwell® assays (Huang et al. (2008) Blood 112:111-119). However, these cells do not exhibit defective diapedesis. In vivo studies have shown that T cells lacking ABL and ARG have defects in migration to lymphoid organs as well as to sites of inflammation (Gu et al. (2012) Sci. Signal., 5:ra51). Thus, they lack the selective trafficking defects described here. Since ABL kinases typically negatively regulate CRK proteins (Feller et al. (1994) EMBO J., 13:2341-2351), it seems paradoxical that loss of either ABL kinases or CRK adaptors impairs migration. Moreover, it was found that mutating the ABL phosphorylation site in CRKII had no effect on diapedesis. The simplest explanation for this is that ABL kinases do not regulate diapedesis by phosphorylating CRK proteins at their inhibitory sites. Instead, CRK proteins may bring ABL kinases in proximity with other substrates. ABL kinases can phosphorylate CASL (HEF-1) and activate RAP1 in response to chemokine stimulation, thereby promoting T cell migration (Gu et al. (2012) Sci. Signal., 5:ra51). As diagrammed in FIG. 6A, binding of ABL kinases to CRK proteins could provide a feedback loop to facilitate CASL tyrosine phosphorylation. This explains the finding that in CRK/CRKL Dko T cells, CASL tyrosine phosphorylation is almost completely abolished.

The SH2 and SH3 domains of CRKII and CRKL are highly conserved, their interaction specificities are almost identical, and redundancy has been reported in other pathways (Park et al. (2008) J. Neurosci., 28:13551-13562; Antoku et al. (2009) J. Cell Sci., 122:4228-4238; Park et al. (2014) Oncogene 33:5121-5132). However, there is also evidence for unique functions, since mice singly deficient for either CRK or CRKL exhibit severe developmental defects (Guris et al. (2001) Nat. Genet., 27:293-298; Park et al. (2006) Mol. Cell Biol., 26:6272-6782). In T cells, it was found that deletion of either gene alone led to defective diapedesis, with loss of CRKL expression being particularly deleterious. Two possibilities are consistent with this finding: either CRK proteins cannot fully compensate for one another, or the overall expression level of all CRK isoforms is important. In support of the latter idea, it was found that overexpression of any CRK isoform in doubly deficient cells could restore normal function. Thus, CRKI, CRKII, and CRKL play partially overlapping roles in T cell adhesion and migration.

Although CRK/CRKL-deficient T cells can home to lymphoid organs, they show impaired transmigration across a TNF-α-activated endothelium and migrate poorly to sites of inflammation. Notably, CRK/CRKL Dko T cells responded similarly to homing (CCL21, CXCL12) and inflammatory (CXCL10) chemokines, thereby indicating that the difference in migratory capacity is not chemokine receptor signaling. Differences in naive versus previously activated T cells are also unlikely, since effector Th1 cells reached lymphoid organs efficiently. Without being bound by theory, CRK proteins are required for passage across postcapillary venules, but not for crossing HEVs. T cell integrins mediate firm adhesion to the endothelial wall and trigger signaling events within the endothelial cells that induce junctional weakening and promote T cell passage (Vestweber et al. (2010) Curr. Opin. Hematol., 17:230-236; Muller et al. (2014) Am. J. Pathol., 184:886-896). Thus, defective integrin activation in CRK/CRKL-deficient T cells could fail to trigger the appropriate endothelial response. The differences between postcapillary venules and HEVs are not fully understood, but it is clear that HEVs are highly specialized to regulate lymphocyte passage (Mionnet et al. (2011) Blood 118:6115-6122). In particular, HEV junctional complexes are more permeable and they produce factors that trigger distinct T cell signaling events (Pfeiffer et al. (2008) Eur. J. Immunol., 38:2142-2155; Bai et al. (2013) J. Immunol., 190:2036-2048). These HEV specializations may therefore circumvent the need for CRK protein signaling.

In many respects, the migration defects observed in the immune system parallel defects in neuronal migration in the developing mouse cortex. Migrating neurons lacking both CRK and CRKL fail to pass through cortical preplate cells and earlier born neurons, resulting in disruption, and apparent inversion, of cortical layers (Park et al. (2008) J. Neurosci., 28:13551-13562). As in T cell migration, the CRK/CRKL-C3GRAP1 pathway is considered to play critical roles in Reelin-dependent neuronal migration. Therefore, it is possible that CRK and CRKL function to modulate the cell-cell interactions that allow migrating cells to pass through nonmigrating cell boundaries.

The differential migratory behavior of CRK-deficient T cells has important ramifications, since these cells can elicit strong GVL responses (which take place largely in lymphoid tissues) with minimal GVHD. Mice lacking CD18 or CCR7 also exhibit effective GVL activity associated with absent or attenuated GVHD responses (Liang et al. (2008) Blood 111:954-962; Coghill et al. (2010) Blood 115:4914-4922), as do mice lacking PKCθ (Valenzuela et al. (2009) J. Clin. Invest., 119:3774-3786). While these models are superficially similar, closer examination reveals important differences. For example, Ccr7$^{-/-}$ T cells show defects in trafficking to recipient lymph nodes, while Cd18$^{-/-}$ T cells migrate efficiently to lymph nodes but are defective in their ability to enter inflamed skin and GVHD target tissues such as intestine (Liang et al. (2008) Blood 111:954-962; Grabbe et al. (2002) J. Clin. Invest., 109:183-192). PKCθ deficiency was shown to affect GVHD via altered T cell effector function (Valenzuela et al. (2009) J. Clin. Invest., 119:3774-3786), but trafficking may also be affected, since PKCθ is known to regulate RAP1 activation and T cell trafficking in other settings (Letschka et al. (2008) Blood 112:4617-4627 Cannon et al. (2013) PLoS One 8:e78940). CRK-deficient T cells, which migrate efficiently to lymphoid organs but inefficiently to liver in a GVHD model, most closely resemble the Cd18$^{-/-}$ T cells. Additional kinetic analysis of T cell trafficking and target organ damage will be needed to fully understand how CRK protein deficiency affects the balance between GVL and GVHD. Unlike CD18- or CCR7-deficient T cells, T cells lacking CRK proteins retain partial chemokine sensing and integrin function. Thus, trafficking of these cells may be uniquely dependent on density of integrin ligands, presence or absence of shear flow, and other tissue-specific variables.

In the GVL/GVHD model, CRK/CRKL Dko CD8$^+$ T cells eliminated tumor cells as efficiently as WT cells, indicating that in vivo effector function was intact. This was somewhat surprising, since CRK proteins have previously been implicated in TCR signaling (Nolz et al. (2008) J. Cell. Biol., 182:1231-1244: Zhang et al. (2003) J. Biol. Chem., 278:23978-23983), and since decreased adhesion was observed in response to anti-TCR stimulation in CRK/CRKL-deficient T cells (FIG. 2A). In preliminary studies, defects in T cell activation or proliferation were not observed, but the strong stimuli used (anti-TCR or superantigen in vitro, alloantigen in vivo) may mask a role for CRK family proteins.

The findings presented herein identify CRK proteins as therapeutic targets for disrupting deleterious T cell trafficking to inflamed tissues, including GVHD target organs. Related strategies based on blocking integrins or chemokine receptors have shown promise in chronic inflammatory diseases such as inflammatory bowel disease and multiple sclerosis (Lobatón et al. (2014) Aliment Pharmacol. Ther., 39:579-594; Cross et al. (2014) J. Intern. Med., 275:350-363), as well as GVHD (Reshef et al. (2012) N. Engl. J. Med., 367:135-145), but because the initiation and end points of the signaling cascade are targeted, multiple facets of the immune response are compromised. As intermediates in the pathway, CRK and CRKL are valuable targets with more confined effects. In particular, targeting CRK proteins in human donor T cells could reduce morbidity while maintaining efficient GVL responses in allogeneic hematopoietic stem cell transplant recipients.

Crk family proteins have not previously been identified as therapeutic targets for GVHD. Cell penetrating peptides that block the interaction between the CrkL SH3 domain and BCR-Abl have been found to block proliferation of CML cells and similar peptides block the invasiveness of lung cancer cells (Kardinal et al. (1999) Ann. NY Acad. Sci., 886:289-92; Pezeshkpour et al. (2013) Genes Cancer, 4:315-24; Posern et al. (1998) Oncogene, 16:1903-12). The idea of inhibiting lymphocyte adhesion and/or migration is being tested for treatment of GVHD, by targeting other molecules such as the chemokine receptor CCR5 (Reshef R. (2012) Clin. Adv. Hematol. Oncol., 10:663-5; Reshef et al. (2012) N. Engl. J. Med., 367:135-45). Other studies in animal models have used integrin blockade (Li et al. (2004) Scand. J. Immunol., 59:464-8; Bank et al. (2000) Immunobiology 202:239-53). Further, imatinib has been used to treat GVHD, since imatinib inhibits Abl kinase (Olivieri et al. (2013) 122:4111-8; Olivieri et al. (2009) Blood 114:709-18). Because interfering with Crk protein function selectively inhibits trafficking to sites of inflammation, the instant approach has the ability to selectively impede GVHD, without inhibiting GVL.

In accordance with the instant invention, methods of treating, inhibiting, and/or preventing an autoimmune or inflammatory disease is provided. In a particular embodiment, the methods of the instant invention are used with cancer immunotherapy, particularly with allogeneic transplants such as allogeneic hematopoietic stem cell transplants. In a particular embodiment, the method comprises modulating (e.g., reducing/inhibiting) Crk (CrkI and/or CrkII) and/or CrkL activity and/or levels. In a particular embodiment, the method comprises administering an agent which modulates the activity of Crk (CrkI and/or CrkII) and/or CrkL (e.g., an inhibitory nucleic acid molecule (e.g., siRNA, antisense, shRNA, etc. directed to Crk (CrkI and/or CrkII) and/or CrkL), antibody (e.g., an antibody, particularly an antibody fragment, immunologically specific for Crk (CrkI and/or CrkII) and/or CrkL; e.g., an antibody or antibody fragment linked to a cell penetrating peptide), small molecule inhibitor, proteins, polypeptides, antagonists, etc.). In a particular embodiment, at least CrkL is inhibited. Notably, a single compound or agent may modulate or inhibit Crk (CrkI and/or CrkII) and/or CrkL. In a particular embodiment, the method comprises administering cells (e.g., T cells, blood cells, stem cells, bone marrow cells, hematopoietic stem cells) which lack Crk (CrkI and/or CrkII) and/or CrkL (e.g., have a full or partial deletion of the Crk and/CrkL genes (e.g., by genome editing (e.g., using clustered, regularly interspaced, short palindromic repeat (CRISPR)/Cas technology (see, e.g., Sander et al. (2014) Nature Biotech., 32:347-355))) or have had Crk (CrkI and/or CrkII) and/or CrkL reduced or inhibited (e.g., through the administration of at least one Crk (CrkI and/or CrkII) and/or CrkL modulator). In a particular embodiment, the methods of the instant invention treat, inhibit, and/or prevent graft versus host disease (e.g., during hematopoietic stem cell transplant).

Amino acid and nucleotide sequences of human CrkI and CrkII are provided in GenBank Gene ID: 1398. In a particular embodiment, the amino acid or nucleotide sequence of CrkI and CrkII has at least 80%, 85%, 90%, 95%, 97%, 99%, or 100% homology or identity with a sequence provided in GenBank Gene ID: 1398 or GenBank Accession No. NM_005206.4; NP_005197.3: NM_016823.3; or NP_058431.2. An example of an amino acid sequence of CrkI is:

```
                                              (SEQ ID NO: 3)
  1 MAGNFDSEER SSWYWGRLSR QEAVALLQGQ RHGVFLVRDS
    STSPGDYVLS

51 VSENSRVSHY IINSSGPRPP VPPSPAQPPP GVSPSRLRIG
    DQEFDSLPAL

101 LEFYKIHYLD TTTLIEPVSR SRQGSGVILR QEEAEYVRAL
    FDFNGNDEED

151 LPFKKGDILR IRDKPEEQWW NAEDSEGKRG MIPVPYVEKY
    RPASASVSAL

201 IGGR.
```

An example of an amino acid sequence of CrkII is:

```
                                              (SEQ ID NO: 4)
  1 MAGNFDSEER SSWYWGRLSR QEAVALLQGQ RHGVFLVRDS
    STSPGDYVLS

51 VSENSRVSHY IINSSGPRPP VPPSPAQPPP GVSPSRLRIG
    DQEFDSLPAL

101 LEFYKIHYLD TTTLIEPVSR SRQGSGVILR QEEAEYVRAL
    FDFNGNDEED

151 LPFKKGDILR IRDKPEEQWW NAEDSEGKRG MIPVPYVEKY
    RPASASVSAL

201 IGGNQEGSHP QPLGGPEPGP YAQPSVNTPL PNLQNGPIYA
    RVIQKRVPNA

251 YDKTALALEV GELVKVTKIN VSGQWEGECN GKRGHFPFTH
    VRLLDQQNPD

301 EDFS.
```

Amino acid and nucleotide sequences of human CrkL are provided in GenBank Gene ID: 1399. In a particular embodiment, the amino acid or nucleotide sequence of CrkL has at least 80%, 85%, 90%, 95%, 97%, 99%, or 100% homology or identity with a sequence provided in GenBank Gene ID: 1399 or GenBank Accession No. NM_005207.3 or NP 005198.1. An example of an amino acid sequence of CrkL is:

```
                                              (SEQ ID NO: 5)
  1 MSSARFDSSD RSAWYMGPVS RQEAQTRLQG QRHGMFLVRD
    SSTCPGDYVL

51 SVSENSRVSH YIINSLPNRR FKIGDQEFDH LPALLEFYKI
    HYLDTTTLIE

101 PAPRYPSPPM GSVSAPNLPT AEDNLEYVRT LYDFPGNDAE
    DLPFKKGEIL

151 VIIEKPEEQW WSARNKDGRV GMIPVPYVEK LVRSSPHGKH
    GNRNSNSYGI

201 PEPAHAYAQP QTTTPLPAVS GSPGAAITPL PSTQNGPVFA
    KAIQKRVPCA

251 YDKTALALEV GDIVKVTRMN INGQWEGEVN GRKGLFPFTH
    VKIFDPQNPD

301 ENE.
```

In a particular embodiment, the modulator (inhibitor) of Crk (CrkI and/or CrkII) and/or CrkL is an inhibitory nucleic acid molecule (e.g., siRNA, antisense, shRNA, and the like). In a particular embodiment, the modulator is an siRNA or shRNA directed against Crk (CrkI and/or CrkII) and/or CrkL. In a particular embodiment, the siRNA or shRNA targets 5'-GTGGAGTGATTCTCAGGCA-3' (SEQ ID NO: 1; CrkI/II) or 5'-GTTACACACTGCTTACCCT-3' (SEQ ID NO: 2; CrkL). In a particular embodiment, the siRNA or shRNA comprises a nucleotide sequence having at least 80%, 85%, 90%, 95%, 97%, 99%, or 100% homology or identity with SEQ ID NO: 1 or SEQ ID NO: 2 (the RNA form).

Chemically modified siRNA or shRNA molecules may be employed in the instant invention. Non-limiting examples of such chemical modifications include, without limitation, phosphorothioate internucleotide linkages, 2'-O-methyl ribonucleotides, 2'-deoxy-2'-fluoro ribonucleotides, 2'-deoxy ribonucleotides, universal base nucleotides, 5-C-methyl nucleotides, and inverted deoxyabasic residue incorporation. The chemical modifications desirably preserve the inhibition activity of the unmodified siRNA or shRNA molecule in cells while, at the same time, increasing the serum stability of these compounds or other favorable property of the siRNA or shRNA molecules. U.S. Patent Application Publication No. 20050032733, incorporated herein by reference, provides numerous suitable modifications of siRNA and shRNA molecules.

In a particular embodiment, the siRNA and shRNA are delivered and expressed in cells via a vector, particularly a viral vector. Vectors for the expression of siRNA or shRNA molecules typically employ a strong promoter which may be constitutive or regulated. Such promoters are well known in the art and include, but are not limited to, RNA polymerase II promoters, the T7 RNA polymerase promoter, and RNA polymerase 11 promoters (e.g., U6 and H1; see, e.g., Myslinski et al. (2001) Nucl. Acids Res., 29:2502-09). In a particular embodiment, RNA polymerase II promoters are employed. Examples of expression vectors for expressing the siRNA or shRNA molecules of the invention include, without limitation, plasmids and viral vectors (e.g., adeno-associated viruses (AAVs), adenoviruses, retroviruses, and lentiviruses) (see, e.g., Sui et al. (2002) PNAS 99:5515-5520; Xia et al. (2002) Nature Biotech. 20:1006-1010; Barton and Medzhitov (2002) PNAS 99:14943-14945; Brummelkamp et al. (2002) Science 296:550-553; Devroe and Silver (2002) BMC Biotechnol., 2(1):15; Tiscornia et al. (2003) PNAS, 100:1844-1848; Bot et al. (2005) Blood 106:1147-1153; Moore et al. (2010) Methods Mol. Biol., 629: 141-158).

In a particular embodiment, the modulator (inhibitor) of Crk (CrkI and/or CrkII) and/or CrkL is an inhibitory peptide or protein (e.g., a dominant negative polypeptide). In a particular embodiment, the inhibitory peptide or protein comprises an isolated SH2 domain or SH3 domain from Crk (CrkI and/or CrkII) and/or CrkL, as described hereinabove. In a particular embodiment, the inhibitory peptide or protein is a proline rich peptide. In a particular embodiment, the SH2 domain of CrkI is amino acids 5-122 of SEQ ID NO: 3, the SH2 domain of CrkII is amino acids 5-122 of SEQ ID NO: 4, and the SH2 domain of CrkL is amino acids 6-106 of SEQ ID NO: 5. In a particular embodiment, the SH3 domain of CrkI is amino acids 135-189 of SEQ ID NO: 3, the SH3 domain of CrkI is amino acids 135-189 of SEQ ID NO: 4 or 237-293 of SEQ ID NO: 4, and the SH3 domain of CrkL is amino acids 126-180 of SEQ ID NO: 4 or 237-293 of SEQ ID NO: 5. The inhibitory peptide or protein may comprise an amino acid sequence having at least 80%, 85%, 900/o, 95%, 97%, 99%, or 100% homology or identity with these sequences. In a particular embodiment, the inhibitory peptide or protein comprises a full length Crk (CrkI and/or CrkII) and/or CrkL, as described hereinabove, wherein the SH2 or SH3 domain comprises a mutation, such as one described herein. In a particular embodiment, the inhibitory peptide or protein comprises a full length Crk (CrkI and/or CrkII) and/or CrkL, as described hereinabove, wherein Crk (CrkI and/or CrkII) comprises a mutation at R38 (e.g., with a non-basic amino acid; e.g., R38K) or W169 (e.g., W169K). The inhibitory peptide or protein may be conjugated or linked to a cell penetrating peptide. In a particular embodiment, the inhibitory peptide or protein is delivered to a cell via a vector (e.g., a viral vector) comprising a nucleic acid molecules encoding for the inhibitory peptide or protein. Examples of isolated SH2 and SH3 peptides are described, for example, in Kardinal et al. (1999) Ann. NY Acad. Sci., 886:289-92; Pezeshkpour et al. (2013) Genes Cancer, 4:315-24: and Posern et al. (1998) Oncogene, 16:1903-12.

As stated hereinabove, the instant invention provides compositions and methods for the inhibition, treatment, and/or prevention of autoimmune diseases and/or inflammatory diseases. In a particular embodiment, the disease is graft versus host disease. In a particular embodiment, the compositions and methods of the instant invention are used when a patient receives a transplant (e.g., an allogeneic transplant), particularly with regard to cancer immunotherapy (e.g., for treating leukemias and lymphomas, particularly with allogeneic hematopoietic stem cell transplant. In a particular embodiment, the methods further comprise administering at least one anti-inflammatory agent and/or immunosuppressant. The agents may be administered consecutively (before or after) and/or at the same time (concurrently). The agents may be administered in the same composition or in separate compositions.

As used herein, the term "autoimmune disease" refers to the presence of an autoimmune response (an immune response directed against an auto- or self-antigen) in a subject. Autoimmune diseases include diseases caused by a breakdown of self-tolerance such that the adaptive immune system responds to self antigens and mediates cell and tissue damage. Examples of autoimmune disease include, without limitation, acute disseminated encephalomyelitis (ADEM), alopecia areata, autoimmune angioedema, autoimmune aplastic anemia, autoimmune dysautonomia, autoimmune hepatitis, autoimmune hyperlipidemia, autoimmune immunodeficiency, autoimmune inner ear disease (ATED), autoimmune myocarditis, autoimmune pancreatitis, autoimmune retinopathy, autoimmune thrombocytopenic purpura (ATP), autoimmune thyroid disease, autoimmune urticaria, Behcet's disease, celiac disease, Crohn's disease, Cogans syndrome, dermatomyositis, goodpasture's syndrome, Graves' disease, Guillain-Barre syndrome, Hashimoto's encephalitis, Hashimoto's thyroiditis, idiopathic thrombocytopenic purpura (ITP), insulin-dependent diabetes (type 1), lupus (SLE), multiple sclerosis, myasthenia gravis, narcolepsy, pemphigus, pernicious anemia, polymyositis, primary biliary cirrhosis, psoriasis, psoriatic arthritis, rheumatic fever, rheumatoid arthritis, Sjogren's syndrome, transverse myelitis, ulcerative colitis, vasculitis, and Wegener's granulomatosis (Granulomatosis with Polyangiitis (GPA)).

As used herein, an "inflammatory disease" refers to a disease caused by or resulting from or resulting in inflammation. The term "inflammatory disease" may also refer to a dysregulated inflammatory reaction that causes an exaggerated response by macrophages, granulocytes, and/or T-lymphocytes leading to abnormal tissue damage and cell death. An "inflammatory disease" can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, psoriasis, cystic fibrosis, rheumatoid arthritis, inflammatory bowel disease, Crohn's Disease, ulcerative colitis, inflammatory dermatitis, encephalitis, allograft rejection, graft versus host disease, vasculitis, inflammatory arthritis, and myocarditis.

In a particular embodiment, the disease or disorder being treated is graft versus host disease (e.g., comprising an immune attack on the recipient by cells from a donor (allogeneic cells)). Typically, the transplanted tissue is blood (e.g., blood cells), stem cells (e.g., hematopoietic stem cells), or bone marrow. In a particular embodiment, the subject being treated is receiving an allogeneic transplant of cells (e.g., blood cells, stem cells, etc.) for the treatment of leukemia and/or lymphoma. In a particular agent, the Crk (CrkI and/or CrkII) and/or CrkL modulator is administered (e.g., directly or via a vector) to the cells ex vivo prior to the administration to the subject. In a particular embodiment, the instant invention encompasses cancer immunotherapy methods (e.g., treating leukemia or lymphoma) comprising the administration of a Crk (CrkI and/or CrkII) and/or CrkL modulator to the transplant cells (e.g., stem cells, hematopoietic stem cells) prior to administration of the cells to the subject.

Compositions comprising at least one Crk (CrkI and/or CrkII) and/or CrkL modulator are also encompassed by the instant invention. In a particular embodiment, the composition comprises at least one Crk (CrkI and/or CrkII) and/or CrkL modulator and at least one pharmaceutically acceptable carrier. The composition may further comprise at least one other therapeutic compound for the inhibition, treatment, and/or prevention of the disease or disorder to be treated (see, e.g., hereinabove). Alternatively, the other therapeutic compound(s) may be contained within a separate composition(s) with at least one pharmaceutically acceptable carrier. The present invention also encompasses kits comprising a first composition comprising at least one Crk (CrkI and/or CrkII) and/or CrkL modulator and a second composition comprising at least one other therapeutic compound for the inhibition, treatment, and/or prevention of the disease or disorder to be treated. The first and second compositions may further comprise at least one pharmaceutically acceptable carrier.

As explained hereinabove, the compositions of the instant invention are useful for treating an inflammatory and/or autoimmune disease or disorder. A therapeutically effective amount of the composition may be administered to the subject. The dosages, methods, and times of administration are readily determinable by persons skilled in the art, given the teachings provided herein.

The Crk (CrkI and/or CrkII) and/or CrkL modulators as described herein will generally be administered to a patient as a pharmaceutical preparation. The term "patient" as used herein refers to human or animal subjects. These Crk (CrkI and/or CrkII) and/or CrkL modulators may be employed therapeutically, under the guidance of a physician for the treatment of the indicated disease or disorder.

The pharmaceutical preparation comprising the Crk (CrkI and/or CrkII) and/or CrkL modulators of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The dose and dosage regimen of a Crk (CrkI and/or CrkII) and/or CrkL modulator according to the invention that is suitable for administration to a particular patient may be determined by a physician considering the patient's age, sex, weight, general medical condition, and the specific condition and severity thereof for which the antibody is being administered. The physician may also consider the route of administration of the antibody, the pharmaceutical carrier with which the antibody may be combined, and the antibody's biological activity.

Selection of a suitable pharmaceutical preparation depends upon the method of administration chosen. For example, the Crk (CrkI and/or CrkII) and/or CrkL modulators of the invention may be administered by direct injection into any desired tissue or into the surrounding area. In this instance, a pharmaceutical preparation comprises the Crk (CrkI and/or CrkII) and/or CrkL modulators dispersed in a medium that is compatible with the target tissue.

Crk (CrkI and/or CrkII) and/or CrkL modulators may be, for example, administered parenterally, by intravenous injection into the blood stream, or by subcutaneous, intramuscular or intraperitoneal injection. Pharmaceutical preparations for parenteral injection are known in the art. If parenteral injection is selected as a method for administering the antibodies, steps must be taken to ensure that sufficient amounts of the molecules reach their target cells to exert a biological effect.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the antibody in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of Crk (CrkI and/or CrkII) and/or CrkL modulators may be determined by evaluating the toxicity of the modulators in animal models. Various concentrations of pharmaceutical preparations may be administered to murine models of the disease or disorder and the minimal and maximal dosages may be determined based on the results and side effects as a result of the treatment. Appropriate dosage unit may also be determined by assessing the efficacy of the treatment in combination with other standard drugs. The dosage units of Crk (CrkI and/or CrkII) and/or CrkL modulators may be determined individually or in combination with another treatment.

The pharmaceutical preparation comprising the Crk (CrkI and/or CrkII) and/or CrkL modulators may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The methods of the instant invention may further comprise monitoring the disease or disorder in the subject after administration of the composition(s) of the instant invention to monitor the efficacy of the method. For example, the subject may be monitored for cancer remission or elimination and/or the subject may be monitored for severity of GVHD.

Definitions

The singular forms "a," "an," and "the" include plural referents unless the context clearly dictates otherwise.

The terms "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, preservative, antioxidant, solubilizer, emulsifier, adjuvant, excipient, bulking substances, auxilliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described, for example, in "Remington's Pharmaceutical Sciences" by E. W. Martin.

The term "treat" as used herein refers to any type of treatment that imparts a benefit to a patient suffering from an injury, including improvement in the condition of the patient (e.g., in one or more symptoms), delay in the progression of the condition, etc.

As used herein, the term "prevent" refers to the prophylactic treatment of a subject who is at risk of developing a condition and/or sustaining an injury, resulting in a decrease in the probability that the subject will develop conditions associated with the injury.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated traumatic brain injury in a patient.

As used herein, the term "subject" refers to an animal, particularly a mammal, particularly a human.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The phrase "small, interfering RNA (siRNA)" refers to a short (typically less than 30 nucleotides long, particularly 12-30, 17-25, or 18-22 nucleotides in length) double stranded RNA molecule. Typically, the siRNA modulates the expression of a gene to which the siRNA is targeted (e.g., the siRNA comprises a sequence complementary to the targeted gene or sequence). Methods of identifying and synthesizing siRNA molecules are known in the art (see, e.g., Ausubel et al. (2006) Current Protocols in Molecular Biology, John Wiley and Sons, Inc). As used herein, the term siRNA may include short hairpin RNA molecules (shRNA). Typically, shRNA molecules consist of short complementary sequences (the siRNA molecule) separated by a small loop sequence (e.g., about 3-20, 3-15, or 4-11 nucleotides in length), wherein one of the sequences is complimentary to the gene target, shRNA molecules are typically processed into an siRNA within the cell by endonucleases. Exemplary modifications to siRNA molecules are provided in U.S. Application Publication No. 20050032733. Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and RNA polymerase III promoters (e.g., U6 and H1; see, e.g., Myslinski et al. (2001) Nucl. Acids Res., 29:2502-09).

"Antisense nucleic acid molecules" or "antisense oligonucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucleotide synthesis according to standard methods.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule. Antibody fragments include, without limitation, immunoglobulin fragments including, without limitation: single domain (Dab; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody. The antibody may also be a protein (e.g., a fusion protein) comprising at least one antibody or antibody fragment.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

The terms "immunosuppressant" and "immunosuppressive agent", as used herein, include compounds or compositions which suppress immune responses or the symptoms associated therewith. Immunosuppressant include, without limitation, purine analogs (e.g., azathioprine), methotrexate, cyclosporine (e.g., cyclosporin A), cyclophosphamide, leflunomide, mycophenolate (mycophenolate mofetil), steroids (e.g., glucocorticoid, corticosteroid), methylprednisone, prednisone, non-steroidal anti-inflammatory drug (NSAID), chloroquine, hydroxycloroquine, chlorambucil. CD20 antagonist (e.g., rituximab, ocrelizumab, veltuzumab or ofatumumab), abatacept, a TNF antagonist (e.g., infliximab, adalimumab, etanercept), macrolides (e.g., pimecrolimus, tacrolimus (FK506), and sirolimus), dehydroepiandrosterone, lenalidomide, a CD40 antagonist (e.g., anti-CD40L antibodies), abetimus sodium, BLys antagonists (e.g., anti-BLyS (e.g., belimumab), dactinomycin, bucillamine, penicillamine, leflunomide, mercaptopurine, pyrimidine analogs (e.g., cytosine arabinoside), mizoribine, alkylating agents (e.g., nitrogen mustard, phenylalanine mustard, buslfan, and cyclophosphamide), folic acid antagonsists (e.g., aminopterin and methotrexate), antibiotics (e.g., rapamycin, actinomycin D, mitomycin C, puramycin, and chloramphenicol), human IgG, antilymphocyte globulin (ALG), antibodies (e.g., anti-CD3 (OKT3), anti-CD4 (OKT4), anti-CD5, anti-CD7, anti-IL-2 receptor (e.g., daclizumab and basiliximab), anti-alpha/beta TCR, anti-ICAM-1, muromonab-CD3, anti-IL-12, alemtuzumab and antibodies to immunotoxins), and derivatives and analogs thereof.

As used herein, an "anti-inflammatory agent" refers to compounds for the treatment of an inflammatory disease or the symptoms associated therewith. Anti-inflammatory agents include, without limitation, non-steroidal anti-inflammatory drugs (NSAIDs; e.g., aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (e.g., prednisone, betamethasone, budesonide, cortisone, dexamethasone, hydrocortisone, methylprednisolone, prednisolone, tramcinolone, and fluticasone), rapamycin, acetaminophen, glucocorticoids, steroids, beta-agonists, anticholinergic agents, methyl xanthines, gold injections (e.g., sodium aurothiomalate), sulphasalazine, and dapsone.

A "vector" is a genetic element, such as a plasmid, cosmid, bacmid, phage or virus, to which another genetic sequence or element (either DNA or RNA) may be attached so as to bring about the replication and/or expression of the attached sequence or element. A vector may be either RNA or DNA and may be single or double stranded. An "expression operons" refers to a nucleic acid segment that may possess transcriptional and translational control sequences, such as promoters, enhancers, translational start signals, polyadenylation signals, terminators, and the like, and which facilitate the expression of a polynucleotide or a polypeptide coding sequence in a host cell or organism.

A "cell-penetrating peptide" refers to a peptide which can transduce another peptide, protein, or nucleic acid into a cell in vitro and/or in vivo—i.e., it facilitates the cellular uptake of molecules. Examples of cell penetrating peptides include, without limitation, Tat peptides, penetratin, transportan, and the like.

The following examples describe illustrative methods of practicing the instant invention and are not intended to limit the scope of the invention in any way.

EXAMPLE 1

Methods

Mice

Mice homozygous for both floxed Crk and Crkl genes (Park et al. (2008) J. Neurosci., 28:13551-13562) were crossed with Cd4-Cre transgenic (Tg) mice on the C57BL/6 background (Taconic) to generate mice with deletion of Crk and Crkl late in T cell development. Some of these mice were further crossed to Rosa26-YFP mice (The Jackson Laboratory) to monitor Cre expression (Srinivas et al. (2001) BMC Dev. Biol., 1:4). WT littermates were used as controls. BALB/c and B6/SJL mice were obtained from the Jackson Laboratory.

Cell Isolation and Culture

Naive CD4$^+$ T cells were purified from lymph nodes and/or spleen by negative selection (Huang et al. (2008) Blood 112:111-119). To generate preactivated T cells, freshly isolated CD4$^+$ T cells were stimulated in 24-well plates coated with 1 pgiml anti-CD3 (2C11, BioXCell) and anti-CD28 (PV-1, BioXCell) at 37° C. Two days after stimulation, T cells were split into fresh non-stimulating wells and cultured for an additional 4-7 days. Experiments were performed 4-6 days after removal from anti-CD3/anti-CD28. Th1 cells were generated (Austrup et al. (1997) Nature 385:81-83). Briefly, CD4+ T cells were seeded on anti-CD3- and anti-CD28-coated plates and cultured in the presence of 20 ng/ml IFN-γ (eBioscience), 5 ng/ml IL-12 (R&D Systems), and 1 µg/ml anti-IL-4 (Biological Resource Branch, National Cancer Institute, Frederick, Md.) for 3 days. Cells were then transferred to new plates and supplemented with the same concentrations of cytokines and 25 IU/ml rhIL-2 (Hoffmann-La Roche Inc.).

Retroviral Transduction cDNAs encoding CRKI, CRKII, CRKL, CRKII R38K, CRKII R169K, or CRKII Y221F were cloned into MigR1, which co-expresses eGFP from a bicistronic message, and production of high-titer retroviral supernatant in 293T cells (Pear et al. (1998) Blood 92:3780-3792). Primary CD4+ T cells were transduced after 2 days of plate-bound anti-CD3 and anti-CD28 stimulation. Cells were collected and re-seeded as $2.5 \times 10^5$/well in 24-well plates, and spin infected with freshly prepared retroviral supernatants, containing 2 µg/ml Polybrene (Sigma-Aldrich) at 2,000 rpm for 90 minutes at 25° C. After the spin infection, cells were washed and cultured with 100 IU/ml IL-2 for an additional 5 days in the absence of stimulation.

Reagents, Antibodies, and Flow Cytometry

All reagents were from Sigma-Aldrich unless otherwise specified. Antibodies against CRK, RAP1, and RAC1 were from BD Biosciences. Anti-phospho-Erk p42/p46 was from Cell Signaling Technology Inc. Anti-CRKL (C-20) was from Santa Cruz Biotechnology. Anti-ZAP70 has been described (Huang et al. (2005) J. Biol. Chem., 280:23576-23583). For flow cytometry, single-cell suspensions were stained with the following fluorescently conjugated antibodies from BioLegend: B220 (RA3-6B2), CD25 (PC61), CD29 (HM_1-1), CD4 (RM4-5), CD44 (1M7), CD45.1 (A20), CD62L (MEL-14), CD69 (H1.2F3), CD8 (clone 53-6.7), and CXCR3 (CXCR3-173) or with CD11a (121/7, BD Biosciences). Intracellular labeling with mouse anti-CRK, followed by PE-conjugated anti-mouse IgG (BioLegend), and rabbit anti-CRKL, followed by Alexa Fluor 488-conjugated anti-rabbit IgG (Invitrogen), or allophycocyanin-conjugated IFN-γ (XMG1.2, eBioscience) was performed (Bird et al. (1998) Immunity 9:229-237). For intracellular labeling of IFN-γ, T cells were stimulated with PMA (50 ng/ml) and ionomycin (500 ng/ml) for 4 hours. Two hours prior to harvest, brefeldin A (1 µg/ml) was added to the cells. Cells were analyzed by flow cytometry using a FACSCalibur or LSR II (BD Biosciences). Analysis was carried out using FlowJo (Tree Star).

To detect CCR7 surface expression, cells were incubated with mouse CCL19-Fc (eBioscience) for 30 minutes at 4° C. washed, and incubated with biotin-conjugated anti-human IgG (Fc fragment specific, Jackson ImmunoResearch Laboratories) for 20 minutes. Cells were washed again, stained with PE-conjugated streptavidin (eBioscience), and analyzed by flow cytometry.

RAP1, CDC42, and RAC1 Pull-Down Assay and C3G and CASL Immunoprecipitation

T cells were stimulated with 10 nM CCL21, lysed, and subjected to GST-RalGDS (for RAP1) or GST-PakRBD (for RAC1 and CDC42) precipitation (Huang et al. (2008) Blood 112:111-119). $1 \times 10^7$ T cell blasts per condition were used for each RAP1/CDC42 assay, and $5 \times 10^6$ cells per condition were used for each RAC1 assay. C3G immunoprecipitation was performed (Nolz et al. (2008) J. Cell. Biol., 182:1231-1244). Briefly, cells were chemokine stimulated, and lysates were incubated with GST-CRKL-nSH3 recombinant protein (Mayo Clinic, Rochester, Minn.), followed by incubation with glutathione agarose resin (Thermo Scientific). For CASL immunoprecipitation, chemokine-activated cell lysates were incubated with anti-CASL (2G9, Abeam). The precipitates were immunoblotted for phospho-tyrosine (4G10, Millipore).

Adhesion and Chemotaxis Assay

Adhesion assays were performed as described (Huang et al. (2005) J. Biol. Chem., 280:23576-23583) with some modifications. Ninety-six well plates were coated with various doses of integrin ligands at 4° C. overnight, then blocked with 2.5% BSA at room temperature for 1 hour. For ICAM-1, 96-well plates (Nunc MaxiSorp plate, Thermo Scientific) were coated with 100 µl of 0.5 µg/ml or 1 µg/ml recombinant mouse ICAM-1 (R&D Systems) per well. For fibronectin, 96-well plates (Costar plate 3596) were coated with 100 µl of 3 or 10 µg/ml human fibronectin (R&D Systems) per well. T cells were labeled with 2.5 pgiml Calcein-AM (Invitrogen) at 37CC for 30 minutes, washed, and resuspended at $2 \times 10^6$/ml in PBS containing 2.5% BSA, $Ca^{2+}$, and $Mg^{2+}$. Fifty microliters of cells were added to each well and left to settle for 20 minutes on ice, followed by the addition of 10 nM chemokine, 1 µg/ml anti-CD3 (500A2, BD Biosciences), or 10 ng/ml PMA. Cells were warmed in a 37° C. water bath for 10 minutes. The unbound cells were washed off and adherent cells were measured using a Synergy HT Multi-Mode microplate reader (Biotek). The percentage of T cell adhesion was calculated as fluorescence of adherent cells/total fluorescence of cells added to each microplate well.

Chemotaxis assays were performed as described (Huang et al. (2008) Blood 112:111-119). Ninety-six-well ChemoTx chambers (3-µm pore size, Neuroprobe) were filled with buffer with or without 10 nM chemokines in the bottom wells, and cells were applied to the upper wells. After 2 hours incubation at 37° C., migrated cells collected from the bottom wells were quantified by flow cytometry.

T Cell Polarization on Fibronectin

Coverslips were acid washed by incubating in 10% $H_2O_2$ in 0.1N HCl and then coated with 50 µg/ml fibronectin in PBS (containing $Mg^{2+}$ and $Ca^{2+}$) for 2 hours at room temperature. $5 \times 10^4$ preactivated CD4+ T cells made from WT or CRK/CRKL Dko mice were added to each coverslip and allowed to adhere for 30 minutes at 37° C. Cells were then fixed using 3% PFA in PBS. In each experiment, at least 50 T cells of each genotype were blindly scored based on whether they were unpolarized (circular cells) or polarized (cells with an obvious leading edge and uropod).

Diapedesis Assay $4 \times 10^5$ 3B-11 endothelial cells (ATCC) were plated onto 35-mm plastic ibiTreat µ-dishes (ibidi) in DMEM with 10% FBS and incubated at 37° C. overnight. Media was then replaced with DMEM containing 0.25% FBS. After 8-10 hours, some dishes were treated with 50 ng/ml TNF-α (PeproTech) to induce VCAM-1 and ICAM-1 upregulation. $2 \times 10^5$ WT or CRK/CRKL Dko preactivated $CD4^+$ T cells were added to the 3B-11 monolayers. In some experiments, WT and CRK/CRKL Dko T cells were stained with 2 µM CFSE or 10 µM CellTracker Orange CMTMR (both from Invitrogen) the day before imaging. Fluorescently labeled WT and CRK/CRKL Dko T cells were mixed 1:1 and added to the 3B-11 monolayers. Cells were maintained at 37° C. during imaging. Images were collected every 30 seconds for 2 hours on an Axiovert 200M microscope (Zeiss) using a ×20 LR objective and a Coolsnap FX-HQ camera (Roper Scientific). The T cells that underwent transendothelial migration were tracked and determined as percentage of total analyzed T cells.

As an alternative diapedesis assay, Transwell® (plate (Costar 3421) inserts were coated with 0.1% gelatin, and 3B-11 cells were grown on the insert overnight. The next day, 3B-11 cells were treated with 10-50 ng/ml TNF-α for 12-16 hours. T cells were then added to the insert, and 2 hours later, T cells that migrated through the inserts were collected and analyzed by flow cytometry.

3D Chemotaxis 3D chemotaxis was performed using tissue culture-treated μ-slide chemotaxis 3D chambers (ibidi). To produce collagen gels for migration studies, bovine skin collagen type I (Pure-Col, Advanced BioMatrix) was used at 1.6 mg/ml to make 5-μm-size pores (Banerjee et al. (2008) Lab. Invest., 88:196-206). The collagen solution was neutralized and mixed with T cell blasts according to the manufacturer's instructions, to yield a final concentration of 1×DMEM, 1.2% FBS, 0.3% NaHCO$_3$, and 1.6×10$^6$ T cells/ml. The collagen-cell suspension was loaded into the chambers and allowed to polymerize at 37° C., 5% CO$_2$ for 1 hour. 80 nM CCL19 or CCL21 in DMEM containing 1% FBS was added to one reservoir of each chamber, and DMEM containing 1% FBS was added to the opposite reservoir. Chambers were incubated for 30 minutes at 37° C. to allow establishment of a linear chemokine gradient. Multiple chemotaxis chambers were visualized in parallel using a ×5 objective on a Zeiss Axiovert 200 M inverted microscope equipped with an automated stage and a 37° C. environmental chamber. Images were collected at 1-minute intervals for 4 hours, using Slidebook 5.0 (Intelligent Imaging Innovations). Analysis was performed using the ibidi chemotaxis plugin for ImageJ, as described (Zengel et al. (2011) BMC Cell. Biol., 12:21). Analysis was restricted to motile T cells by eliminating objects that were present in the field of view for less than 30 minutes and that displaced less than 15 μm. Population analysis of unfiltered data did not reveal significant differences in the proportion of motile T cells in WT and CRK/CRKL Dko samples.

In Vivo Migration Assays

For T cell homing, purified CD4+ T cells from WT or CRK/CRKL Dko mice were activated with anti-CD3 and anti-CD28 for 3 days and rested for 4 days.

These rested T cells were stained with CFSE or CMTMR and mixed 1:1, and a total of 1×10$^7$ to 2×10$^7$ cells was injected intravenously into sex-matched C57BL/6 recipient mice. One hour after injection, recipient mice were euthanized, and blood, lymph nodes, and spleen were collected. The ratios of Dko to WT CD4+ T cells were measured. To test naive T cell homing, peripheral lymph node (subiliac, auxiliary, and cervical) cells were collected from B6.SJL (CD45.1+) and CRK/CRKL Dko Rosa-YFP (CD45.2) mice, mixed at a ratio of 1:1, and injected into C57BL/6 recipient mice. Simultaneously, peripheral lymph node cells isolated from WT littermate control mice (CD45.2+) were labeled with 0.2 μM CFSE, mixed with B6.SJL cells at a ratio of 1:1, and injected into different recipient mice. One hour after adoptive transfer, recipient mice were euthanized; blood, lymph nodes, and spleens were collected; and the frequency of transferred naive T cells (CD44$^{lo}$, CD62L$^{hi}$) was quantified by flow cytometry. The inflammation assay was performed as described (Austrup et al. (1997) Nature 385:81-83). To induce a cutaneous inflammation, 0.5% DNFB was dissolved in acetone-olive oil (4:1) and applied to recipient mice (C57BL/6 mice) by skin painting on day −21 and day −20. On day −1, recipient mice were challenged with 0.3% DNFB. WT or CRK/CRKL Dko Th1 cells were labeled with 1 μM CFSE or 5 μM CMTMR and mixed at a ratio of 1:1, and 1×10$^7$ to 2×10$^7$ T cells were injected intravenously. Twenty-four hours after adoptive transfer, recipient mice were euthanized; blood, lymph nodes, spleens, and skin were collected; and the frequency of transferred WT and CRK/CRKL Dko T cells was quantified by flow cytometry. All inflammation experiments were performed side-by-side with reciprocal staining. Each in vivo experiment was conducted with pooled donor cells from at least 3 mice per genotype to minimize donor-to-donor variations. The migration index was calculated as Dko adoptively transferred/WT adoptively transferred, normalized to Dko input/WT input.

GVHD and GVL

For GVHD, CD4+ T cells were purified from WT or CRK/CRKL Dko mice, mixed with T cell-depleted bone marrow (TCD-BM) cells that were prepared from C57BL/6 mice, and injected into lethally irradiated BALB/c mice (8 Gy×1). Body weight and GVHD scores were assessed as described (Anderson et al. (2005) Blood 105:2227-2234). For GVL, purified CD8+ T cells from WT or CRK/CRKL Dko mice were mixed with TCD-BM and A20 cells that express luciferase and injected into irradiated BALB/c mice. The bioluminescent signal intensity was determined after intraperitoneal injection of 4.5 mg Firefly D-luciferin (Biosynth) using the IVIS 200 system (Xenogen). The survival and body weight changes of the recipient mice were assessed.

To assess T cell migration during the GVHD, CD8+ T cells were sorted by flow cytometry from WT or CRK/CRKL Dko mice (CD45.2+, Thy1.1−) and mixed 1:1 with FACS-sorted CD8+ T cells from B6.SJL mice (CD45.1+, Thy1.1−). These CD8+ T cells were injected together with TCD-BM (Thy1.1+) into lethally irradiated BALB/c mice. On day 10-12, the recipient mice were sacrificed, and the spleen and liver were harvested. The ratio of adoptively transferred CD8+ T cells (all H2K$^{b+}$, Thy1.1−) from experimental (WT or Dko, both CD45.2+) versus competitor (B6.SJL, CD45.1+) mice was determined by flow cytometry.

Statistics

Bar graphs represent mean±SD. Data were analyzed using Excel or Prism 5.0 (GraphPad Software). Statistical significance was tested using paired or unpaired 2-tailed Student's t tests or ANOVA as appropriate, with P<0.05 set as a cutoff for significance.

Study Approval

Animals were maintained and procedures were performed with approval of the IACUCs of the Children's Hospital of Philadelphia and the University of Pennsylvania School of Medicine.

Results

Generation and Characterization of T Cell-Specific CRK/CRKL Deficient Mice

To delete the Crk and Crkl genes in mature T cells, mice bearing loxP-flanked Crk and Crkl alleles (Park et al. (2008) J. Neurosci., 28:13551-13562) were bred with Cd4-Cre transgenic mice (Crk$^{fl/fl}$ Crk$^{fl/fl}$ Cd4-Cre mice; hereafter called CRK/CRK Dko mice). Some strains were further crossed to Rosa26-EYFP mice to monitor Cre expression (Srinivas et al. (2001) BMC Dev. Biol., 1:4). Analysis of CRK/CRK Dko Rosa-EYFP mice showed that Cre expression was present in 95% of peripheral CD4+ and CD8+ T cells. Western blotting of purified CD4+ T cells from Dko and WT mice revealed that levels of CRKI, CRKII, and CRKL in the mutant T cells were reduced by at least 95% (FIG. 1A), and flow cytometric analysis confirmed loss of CRK protein expression (FIGS. 1B and 1C).

CRK/CRKL Dko mice were born at Mendelian ratios, and spleen, thymus, and lymph nodes exhibited normal cellularity. Thymocyte populations were similar in WT and Dko mice, indicating that T cell development proceeded normally (FIG. 1D). Peripheral lymphoid organs showed no differences in proportions of CD4+ and CD8+ T cells, naive (CD62L$^{hi}$CD44$^{lo}$), memory (CD62L$^{lo}$CD44$^{hi}$), or activated (CD69$^{hi}$) T cell subsets (FIGS. 1D and 1E). Thus, these mice represented a suitable source of mature CRK/CRKL Dko T cells for functional studies.

CRK/CRKL-deficient T Cells Show Defects in Adhesion and Polarization

Since CRK proteins control adhesion in non-hematopoietic cells (Birge et al. (2009) Cell. Commun. Signal 7:13), it was determined whether integrin-dependent adhesion is defective in CRK/CRKL Dko T cells. On plates coated with ICAM-1, the ligand for the $\beta_2$ integrin LFA-1, WT preactivated CD4$^+$ T cells showed about 10% basal binding, which was increased 2- to 5-fold after stimulation with the chemokines CXCL12 or CCL21, or anti-CD3 (FIG. 2A). CRK/CRKL Dko T cells showed a significant reduction in adhesion to ICAM-1 under both basal and stimulated conditions. Indeed, chemokine stimulation induced almost no increased adhesion in these cells. Treatment with PMA bypassed the defect. This is most likely because the defect in CRK/CRKL Dko cells lies upstream of PKC signaling in the pathway leading to integrin activation, though PKC activation could also drive a parallel pathway (Letschka et al. (2008) Blood 112:4617-4627). Similar adhesion defects were observed in response to fibronectin, a ligand for the $\beta_1$ integrin VLA-4 (FIG. 2B). These defects were not attributable to altered integrin expression, since CRK/CRKL Dko T cells expressed normal surface levels of the CD11a chain of LFA-1 and the CD29 chain of VLA-4 (FIG. 2C).

Binding to integrins induces T cell polarization, a process that sets the stage for motility (Smith et al. (2003) J. Cell Sci., 116:3123-3133). This event, too, was reduced in integrin-stimulated CRK/CRKL Dko cells (FIGS. 2D and 2E). This phenotype does not represent a general polarity defect, since CRK/CRKL Dko T cell blasts formed well-developed uropods in response to anti-CD3anti-CD28 stimulation. Together, these results show that CRK proteins are required for efficient integrin-dependent T cell adhesion and downstream events leading to cell polarity.

CRK and CRKL are Required for Efficient T Cell Chemotaxis

It was then determined whether CRK and CRKL are important for T cell migration using a Transwell®-based chemotaxis assay. As shown in FIGS. 3A and 3B, WT CD4+ T cells chemotaxed efficiently toward both CCL21 and CXCL10, chemokines that signal naive T cell trafficking into lymph nodes (Stein et al. (2000) J. Exp. Med., 191:61-76; Warnock et al. (2000) J. Exp. Med., 191:77-88) and Th1 cell trafficking to sites of inflammation (Groom et al. (2011) Immunol. Cell Biol., 89:207-215), respectively. In contrast, CRK/CRKL Dko T cells displayed 20°/%-50% less migration toward both chemokines. These defects were not due to differences in the surface expression of the relevant chemokine receptors CCR7 and CXCR3 (FIG. 3C). Similar results were obtained with CXCL12, a CXCR4 ligand that cooperates with CCR7 ligands to promote naive T cell trafficking across HEVs (Bai et al. (2009) J. Immunol., 182:1287-1295).

Since 2D migration (including Transwell® assays) involves integrin function, chemotaxis was also tested in 3D collagen gels, where migration is integrin independent (Lämmermann et al. (2008) Nature 453:51-55). Interestingly, CRK/CRKL Dko T cells chemotaxed efficiently toward both CCL19 and CCL21 in this setting (FIG. 3D and Table 1). Comparison of multiple parameters including velocity, directionality, and forward migration index showed no significant differences between mutant and WT cells. Thus, it was conclude that loss of CRK proteins primarily impairs adhesion-dependent T cell migration; chemokine sensing is intact, and the response is sufficient to induce directional migration in settings where integrin-dependent adhesion is not required.

TABLE 1

Chemotaxis in 3D collagen gels.

|  | y Forward migration index | Directionality | Velocity (mean ± SD) |
|---|---|---|---|
| Experiment 1, CCL19 | | | |
| WT | −0.22 | 0.37 | 9.6 ± 3.0 μm/min |
| Dko | −0.22 | 0.32 | 10.8 ± 3.0 μm/min |
| Experiment 2, CCL19 | | | |
| WT | −0.26 | 0.33 | 8.6 ± 2.5 μm/min |
| Dko | −0.25 | 0.33 | 8.3 ± 2.8 μm/min |
| Experiment 3, CCL21 | | | |
| WT | −0.24 | 0.33 | 8.6 ± 3.3 μm/min |
| Dko | −0.28 | 0.33 | 9.1 ± 3.0 μm/min |

CRK/CRKL-deficient T Cells are Defective in Diapedesis

Firm adhesion is a prerequisite for T cells to transmigrate through the endothelial wall (extravasation/diapedesis) (Ley et al. (2007) Nat. Rev. Immunol., 7:678-689). To ask whether CRK proteins regulate diapedesis, T cells were monitored by time-lapse imaging while interacting with endothelial monolayers (untreated, or previously treated with TNF-α to upregulate ICAM-1 and VCAM-1 expression. In this assay, cells that pass through the endothelial monolayer become phase-dark and flattened. FIG. 4A shows a WT T cell undergoing diapedesis and a CRK/CRKL Dko cell that remained on the top of the monolayer. Quantitative analysis revealed that WT T cells showed robust diapedesis across TNF-α-treated endothelia, but CRK/CRKL Dko cells exhibited major defects (FIG. 4B). Similar results were obtained using in vitro generated CRK/CRKL Dko Th1 cells and using an alternate assay in which endothelial cells were grown on Transwell® inserts (FIG. 4C).

CRK and CRKL have Partially Overlapping Function

Since the Transwell® based diapedesis assay showed robust and reproducible defects in CRK/CRKL Dko T cells, this assay was used to test functional redundancy among the 3 CRK isoforms. First, CRK/CRKL Dko CD4+ T cells were retrovirally reconstituted with CRKI, CRKII, or CRKL. As shown in FIG. 4C, ectopic expression of any individual CRK isoform could fully rescue diapedesis, indicating overlapping function among CRK proteins. Retroviral transduction yielded 5- to 10-fold overexpression relative to endogenous protein levels (FIG. 4D), raising the possibility that this result stemmed from CRK protein overexpression. Thus, T cells from CRK or CRKL single knockout mice were also tested. These cells showed no compensatory changes in CRK protein expression. As shown in FIG. 4E, T cells lacking either CRK or CRKL alone showed defective diapedesis. CRKL-deficient T cells showed a more profound defect, similar in magnitude to that in Dko T cells. Thus, it was conclude that CRK and CRKL are both required for optimal T cell diapedesis, with CRKL playing a more prominent role.

CRK and CRKL Selectively Promote Activation of RAP1 and CDC42

It was then determined what molecular pathways are controlled by CRK and CRKL to promote T cell adhesion and migration. No significant differences were observed between CRK/CRKL Dko T cells and WT cells in CCL21- induced ERK phosphorylation (FIG. 5A), demonstrating that by this measure, Dko T cells respond to chemokine receptor stimulation as well as WT T cells. In non-hematopoietic cells, CRK proteins act upstream of C3G and DOCK to regulate activation of the small GTPases RAP1 and RAC1, respectively (Birge et al. (2009) Cell. Commun. Signal., 7:13). Therefore, effector pull-down assays were performed to assess GTPase activation. In WT T cells, RAC1-GTP levels increased within 0.5 minutes after chemokine addition and remained elevated for 2-5 minutes (FIGS. 5A and 5D). The kinetics of RAC1 activation varied somewhat among experiments, precluding averaging of results. Nonetheless, CRK protein deficiency consistently failed to affect the magnitude or the kinetics of RAC1 activation. In contrast, RAP1 activation was attenuated in CRK/CRKL Dko T cells (FIGS. 5A and 5B). Similar defects in RAP1 activation were observed in CRK/CRKL Dko Th1 cells with CXCL10 (FIGS. 5E and 5F). Finally, although CRK proteins have not been previously implicated in activation of CDC42, we also observed blunting of CDC42 activation in CRK/CRKL Dko T cells (FIGS. 5A and 5C). Thus, it was conclude that CRK proteins promote chemokine-induced activation of RAP1 and CDC42, but not RAC1.

CRK and CRKL Coordinate C3G and CASL to Regulate T Cell Diapedesis

Since RAP1 activation was defective in CRK/CRKL Dko T cells, it was determined whether activation of the RAP1 GEF C3G was also perturbed. C3G was isolated from chemokine-stimulated WT and CRK/CRKL Dko T cells based on binding to recombinant CRKL-nSH3 (Nolz et al. (2008) J. Cell Biol., 182:1231-1244), and tyrosine phosphorylation was assessed by immunoblotting. As shown in FIG. 6B, phosphorylation of C3G was blunted in CXCL10-stimulated CRK/CRKL Dko T cells. Similar results were obtained after stimulation with CCL21. Parallel analysis was performed for CASL (CRK-associated substrate in lymphocytes), a critical regulator of T cell migration that interacts with the SH2 domain of CRK proteins (Kanda et al. (1997) Eur. J. Immunol., 27:2113-2117) (FIG. 6A). As shown in FIG. 6C, tyrosine phosphorylation of CASL was almost completely abolished in Dko T cells, indicating that CRK proteins also promote CASL activation.

To further test the functional importance of CRK protein adaptor function, point mutations were made in the SH2 (R38K) or nSH3 (R169K) domain of CRKII to interrupt binding to CASL or C3G, respectively (Shishido et al. (2001) Genes Cells 6:431-440) (FIG. 6A). WT or mutant CRKII proteins were expressed in Dko T cells, and diapedesis was analyzed. As shown in FIG. 6D, diapedesis was rescued by reconstitution with WT CRKII but not with the R38K or the R169K mutants. In some settings, adaptor function of the CRKII SH2 and nSH3 domains is negatively regulated by phosphorylation at Y221; however, it was found that a non-phosphorylatable CRKII Y221F mutant rescued T cell diapedesis no better than WT CRKII protein. Thus, either CRKII-dependent diapedesis is not repressed by phosphorylation or diapedesis is maximal and cannot be further upregulated under the conditions tested. Taken together, these studies show that adaptor function mediated by the SH2 and nSH3 domains of CRK proteins promotes activation of C3G and RAP1 as well as CASL, leading to enhanced T cell diapedesis.

CRK and CRKL are Dispensable for T Cell Homing but are Required for Migration to Sites of Inflammation To test CRK protein function in vivo, homing to lymphoid organs was analyzed. First, resting CD4+T lymphoblasts prepared from WT or CRK/CRKL Dko mice were mixed and injected into recipient mice, and short-term (1 hour) homing to lymphoid organs was assessed by flow cytometry. As shown in FIG. 7A, the ratio of CRK/CRKL Dko to WT T cells was slightly less than 1 in lymph node and spleen and approximately 0.5 in blood. The reason for this diminished ratio is unclear and may reflect aberrant trapping of the mutant cells in non-hematopoietic tissues. Nonetheless, these data show that homing of CRK/CRKL Dko T cells to lymphoid organs is grossly normal. To circumvent the complexities associated with homing of resting T lymphoblasts, homing of naive T cells was also tested. Lymphocytes from CRK/CRKL Dko Rosa-EYFP (CD45.2+) and B6.SJL (CD45.1+) mice were mixed 1:1 and adoptively transferred into WT recipient mice (CD45.2+). To control for the genetic background of CRK/CRKL Dko and SJL mice, parallel experiments were performed using fluorescently labeled cells from WT littermates (CD45.2+), mixed with cells from B6.SJL mice. As shown in FIG. 7B, the homing efficiency of naive CD4+ CRK/CRKL Dko T cells was virtually identical to that of WT T cells. This was also true for naive CD8+ T cells.

Although CRK proteins are not needed for homing to lymphoid organs, they might function in migration to inflamed tissues. To investigate this, a cutaneous delayed-type hypersensitivity model elicited by 2, 4-dinitrofluorobenzene (DNFB) was used to test Th1 entry into an inflamed site (Austrup et al. (1997) Nature, 385:135-145). Naive WT and CRK/CRKL Dko CD4+ T cells were skewed in vitro to become Th1 cells, and did so with equal efficiency (FIG. 7C). WT and Dko Th1 cells were then fluorescently labeled, mixed, and transferred into DNFB-treated recipient mice. Trafficking of transferred cells was analyzed 24 hours later. Consistent with the homing experiments above, CRK/CRKL Dko Th1 cells migrated efficiently to lymphoid tissues. Interestingly, however, the mutant cells showed significantly reduced trafficking to inflamed skin (FIG. 7D). Thus, it was conclude that CRK proteins preferentially promote T cell migration to sites of inflammation in vivo.

CRK/CRKL Dko T Cells Attenuate GVHD while Preserving Donor T Cell-mediated GVL Effects Since CRK proteins were important for migration into inflamed tissues, T cells lacking these proteins would exhibit attenuated GVHD. To test this, allogeneic BM transplantation (B6→BALB/c) were performed with WT or CRK/CRKL Dko CD4+ T cells. Compared with mice receiving BM alone, BM-transplanted mice receiving WT T cells exhibited severe GVHD, characterized by continued weight loss and mortality within 30 days after transplantation (FIG. 8, A-C). In contrast. BM-transplanted mice receiving CRK/CRKL Dko T cells exhibited modest GVHD and weight loss, with 70% of mice surviving until the end of the experiment. These results indicate that CRK proteins play a critical role in GVHD pathogenesis.

Although allogeneic T cells cause unwanted GVHD, they also mediate beneficial effects by eradicating residual leukemia cells, a process known as the GVL effect. Thus, devising ways to separate GVHD and GVL responses is critical for improving allogeneic BM transplant outcomes. One potential strategy involves retaining allogeneic T cells in lymphoid organs where leukemic cells reside, allowing GVL but not GVHD effects to occur (Reshef et al. (2012) N. Engl. J. Med., 367:135-145). Based upon the differential migration of CRK/CRKL Dko T cells, it was hypothesized that these cells might display intact GVL responses with reduced GVHD. To test this, allogeneic BM-transplanted mice were injected with or without purified WT or CRK/

CRKL Dko CD8+ T cells and challenged them with host-type A20 lymphoma cells. BM-transplanted mice receiving lymphoma cells without any T cells exhibited rapid tumor growth and succumbed to the tumor within 2-3 weeks (FIGS. 8D-8G). BM-transplanted mice receiving WT T cells controlled tumor growth but died from GVHD within 30 days. In contrast, BM-transplanted mice receiving CRK/CRKL Dko T cells exhibited an equally potent GVL effect, but with significantly attenuated GVHD. Indeed, all recipients of CRK protein-deficient T cells survived to the end of the experiment. These results indicate that T cells that lacking CRK proteins can control GVHD while preserving beneficial GVL, leading to significantly improved survival of allogeneic BM transplant recipients.

Finally, to ask whether the ability of CRK/CRKL Dko T cells to carry out GVL with minimal GVHD is related to their differential migratory capacity. T cell trafficking in the GVHD model was analyzed using a competitive assay. CD8+ T cells purified from WT or CRK/CRKL Dko mice were mixed with competitor T cells from WT B6.SJL mice and injected together with T cell-depleted BM into allogeneic recipient mice. Ten to 12 days later, the ratios of adoptively transferred WT or Dko CD8+ T cells to competitor CD8+ T cells were compared in spleen and liver. As shown in FIG. 8H, WT and competitor T cells migrated to liver and spleen with similar efficiency, with a ratio near 1 in both tissues. Dko T and competitor T cells also migrated with similar efficiency to spleen, consistent with the results in FIG. 7. In contrast to WT T cells, however, the Dko T cells showed a significant competitive disadvantage in trafficking to liver, a key GVHD target organ. Thus, the attenuated GVHD response we observe in mice transplanted with CRK/CRKL Dko T cells was at least partially attributable to defects in T cell trafficking into GVHD target organs.

EXAMPLE 2

Primary human CD4+ cells were activated with anti-CD3 and anti-CD28 beads for 2 days. The activated T cells were then infected (via spinocculation) with a lentiviral vector having a control short hairpin (sh) RNA (shControl), a CrkI/II shRNA (shCrkI/II), or a CrkL shRNA (shCrkL). The CrkI/II sequence is 5'-GTGGAGTGATTCTCAGGCA-3' (SEQ ID NO: 1) and the CrkL sequence is 5'-GTTACA-CACTGCTTACCCT-3' (SEQ ID NO: 2). Puromycin was added on day 4 and cells were removed from activation and lysed on day 7. As seen in FIGS. 9A and 9B, the CrkI/II shRNA (but not shControl or shCrkL) selectively reduced expression of CrkI and CrkII, but not CrkL. Similarly, the CrkL shRNA (but not shControl or shCrkI/II) selectively reduced expression of CrkL, but not CrkI or CrkII.

Primary human CD4+ cells were activated as described above. On day 9, cells were allowed to adhere to coverslips coated with ICAM alone or ICAM with stromal cell-derived factor 1 (SDF-1). Cells were then surface stained for total lymphocyte function-associated antigen 1 (LFA-1) (using monoclonal antibody TS2/4 (harvested from ATCC hybridoma; TS2/t recognizes an epitope on the β propeller domain of CD11a (αL) only in the assembled αβ heterodimer (Huang et al. (1997) Proc. Natl. Acad. Sci., 94:3162-3167))) and the extended open high affinity confirmation of LFA-1 (using monoclonal antibody m24 (binds the activated I domain of CD18 (β2) after hybrid domain swingout (Schurpf et al. (2011) EMBO J., 30:4712-4727; Chen et al. (2010) PNAS 107:14727-14732))). A cell-by-cell ratio of high affinity LFA-1 to total LFA-1 is provided in FIG. 10B. Cells treated with CrkL shRNA or CrkI/II shRNA exhibited a decreased ratio of high affinity LFA-1 to total LFA-1 compared to cells treated with a control shRNA.

Again, primary human CD4+ cells were activated as above. On day 10, cells were labeled with calcein AM and were allowed to adhere to a 96-well plate coated with ICAM alone or ICAM with SDF-1. Cells were then washed and fluorescence was read on a plate reader. As seen in FIG. 11, CrkL shRNA treatment led to reduced cell adhesion when the plate was coated with ICAM and SDF-1.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for inhibiting graft versus host disease in a subject in need thereof, said method comprising administering a Crk inhibitor and CrkL inhibitor to said subject, wherein said inhibitors are inhibitory nucleic acid molecules, and wherein said method comprises delivering said Crk inhibitor and CrkL inhibitor to cells which are then administered to said subject, wherein said cells comprise hematopoietic stem cells or T cells.

2. The method of claim 1, wherein said Crk inhibitor inhibits CrkI, CrkII, or both isoforms.

3. The method of claim 1, wherein said Crk inhibitor and CrkL inhibitor are delivered to said cells in a composition comprising a Crk inhibitor and CrkL inhibitor and at least one pharmaceutically acceptable carrier.

4. The method of claim 1, wherein said inhibitory nucleic acid molecules are selected from the group consisting of siRNA, shRNA, and antisense molecules.

5. The method of claim 4, wherein said siRNA or shRNA comprise SEQ ID NO: 1 or SEQ ID NO: 2.

6. The method of claim 1, wherein said method further comprises administering at least one anti-inflammatory agent.

7. The method of claim 1, wherein said method further comprises administering at least one immunosuppressant.

8. The method of claim 1, wherein said cells are allogeneic transplant cells.

9. The method of claim 1, wherein said cells are allogeneic T cells.

10. The method of claim 1, wherein said cells are allogeneic hematopoietic stem cells.

11. The method of claim 1, wherein said subject is undergoing cancer immunotherapy.

12. The method of claim 11, wherein said cancer is leukemia or lymphoma.

13. The method of claim 11, wherein said cells are allogeneic hematopoietic stem cells.

14. A method of improving a cancer immunotherapy comprising an allogeneic transplant, said method comprising delivering a Crk inhibitor and CrkL inhibitor to said allogeneic transplant prior to administration to the subject receiving the cancer immunotherapy, wherein said improvement is a reduction in graft versus host disease in said subject,
wherein said inhibitors are inhibitory nucleic acid molecules, and
wherein said allogeneic transplant comprises T cells or hematopoietic stem cells.

15. The method of claim 14, wherein said cancer is leukemia or lymphoma.

16. The method of claim 14, wherein said allogeneic transplant comprises hematopoietic stem cells.

17. The method of claim 14, wherein said allogeneic transplant comprises T cells.

* * * * *

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic sequence

<400> SEQUENCE: 1
gtggagtgat tctcaggca                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic sequence

<400> SEQUENCE: 2
gttacacact gcttaccct                                                      19

<210> SEQ ID NO 3
<211> LENGTH: 204
<212> TYPE: PRT
<213> ORGANISM: Homo sapiens

<400> SEQUENCE: 3

Met Ala Gly Asn Phe Asp Ser Glu Glu Arg Ser Ser Trp Tyr Trp Gly
1               5                   10                  15

Arg Leu Ser Arg Gln Glu Ala Val Ala Leu Leu Gln Gly Gln Arg His
            20                  25                  30

Gly Val Phe Leu Val Arg Asp Ser Ser Thr Ser Pro Gly Asp Tyr Val
        35                  40                  45

Leu Ser Val Ser Glu Asn Ser Arg Val Ser His Tyr Ile Ile Asn Ser
    50                  55                  60

Ser Gly Pro Arg Pro Pro Val Pro Pro Ser Pro Ala Gln Pro Pro Pro
65                  70                  75                  80

Gly Val Ser Pro Ser Arg Leu Arg Ile Gly Asp Gln Glu Phe Asp Ser
                85                  90                  95

Leu Pro Ala Leu Leu Glu Phe Tyr Lys Ile His Tyr Leu Asp Thr Thr
            100                 105                 110

Thr Leu Ile Glu Pro Val Ser Arg Ser Arg Gln Gly Ser Gly Val Ile
        115                 120                 125

Leu Arg Gln Glu Glu Ala Glu Tyr Val Arg Ala Leu Phe Asp Phe Asn
    130                 135                 140

Gly Asn Asp Glu Glu Asp Leu Pro Phe Lys Lys Gly Asp Ile Leu Arg
145                 150                 155                 160

Ile Arg Asp Lys Pro Glu Glu Gln Trp Trp Asn Ala Glu Asp Ser Glu
                165                 170                 175

Gly Lys Arg Gly Met Ile Pro Val Pro Tyr Val Glu Lys Tyr Arg Pro
            180                 185                 190

Ala Ser Ala Ser Val Ser Ala Leu Ile Gly Gly Arg
        195                 200

<210> SEQ ID NO 4
<211> LENGTH: 304
<212> TYPE: PRT
<213> ORGANISM: Homo sapiens

<400> SEQUENCE: 4

Met Ala Gly Asn Phe Asp Ser Glu Glu Arg Ser Ser Trp Tyr Trp Gly
1               5                   10                  15

Arg Leu Ser Arg Gln Glu Ala Val Ala Leu Leu Gln Gly Gln Arg His
            20                  25                  30

Gly Val Phe Leu Val Arg Asp Ser Ser Thr Ser Pro Gly Asp Tyr Val
        35                  40                  45

Leu Ser Val Ser Glu Asn Ser Arg Val Ser His Tyr Ile Ile Asn Ser
    50                  55                  60

Ser Gly Pro Arg Pro Pro Val Pro Pro Ser Pro Ala Gln Pro Pro Pro
65                  70                  75                  80

Gly Val Ser Pro Ser Arg Leu Arg Ile Gly Asp Gln Glu Phe Asp Ser
                85                  90                  95

Leu Pro Ala Leu Leu Glu Phe Tyr Lys Ile His Tyr Leu Asp Thr Thr
            100                 105                 110

```
Thr Leu Ile Glu Pro Val Ser Arg Ser Arg Gln Gly Ser Gly Val Ile
            115                 120                 125

Leu Arg Gln Glu Glu Ala Glu Tyr Val Arg Ala Leu Phe Asp Phe Asn
130                 135                 140

Gly Asn Asp Glu Glu Asp Leu Pro Phe Lys Lys Gly Asp Ile Leu Arg
145                 150                 155                 160

Ile Arg Asp Lys Pro Glu Glu Gln Trp Trp Asn Ala Glu Asp Ser Glu
                165                 170                 175

Gly Lys Arg Gly Met Ile Pro Val Pro Tyr Val Glu Lys Tyr Arg Pro
            180                 185                 190

Ala Ser Ala Ser Val Ser Ala Leu Ile Gly Asn Gln Glu Gly Ser
            195                 200                 205

His Pro Gln Pro Leu Gly Gly Pro Glu Pro Gly Pro Tyr Ala Gln Pro
    210                 215                 220

Ser Val Asn Thr Pro Leu Pro Asn Leu Gln Asn Gly Pro Ile Tyr Ala
225                 230                 235                 240

Arg Val Ile Gln Lys Arg Val Pro Asn Ala Tyr Asp Lys Thr Ala Leu
                245                 250                 255

Ala Leu Glu Val Gly Glu Leu Val Lys Val Thr Lys Ile Asn Val Ser
            260                 265                 270

Gly Gln Trp Glu Gly Glu Cys Asn Gly Lys Arg Gly His Phe Pro Phe
            275                 280                 285

Thr His Val Arg Leu Leu Asp Gln Gln Asn Pro Asp Glu Asp Phe Ser
    290                 295                 300
```

<210> SEQ ID NO 5
<211> LENGTH: 303
<212> TYPE: PRT
<213> ORGANISM: Homo sapiens

<400> SEQUENCE: 5

```
Met Ser Ser Ala Arg Phe Asp Ser Ser Asp Arg Ser Ala Trp Tyr Met
1               5                   10                  15

Gly Pro Val Ser Arg Gln Glu Ala Gln Thr Arg Leu Gln Gly Gln Arg
            20                  25                  30

His Gly Met Phe Leu Val Arg Asp Ser Ser Thr Cys Pro Gly Asp Tyr
        35                  40                  45

Val Leu Ser Val Ser Glu Asn Ser Arg Val Ser His Tyr Ile Ile Asn
    50                  55                  60

Ser Leu Pro Asn Arg Arg Phe Lys Ile Gly Asp Gln Glu Phe Asp His
65                  70                  75                  80

Leu Pro Ala Leu Leu Glu Phe Tyr Lys Ile His Tyr Leu Asp Thr Thr
                85                  90                  95

Thr Leu Ile Glu Pro Ala Pro Arg Tyr Pro Ser Pro Met Gly Ser
            100                 105                 110

Val Ser Ala Pro Asn Leu Pro Thr Ala Glu Asp Asn Leu Glu Tyr Val
            115                 120                 125

Arg Thr Leu Tyr Asp Phe Pro Gly Asn Asp Ala Glu Asp Leu Pro Phe
130                 135                 140

Lys Lys Gly Glu Ile Leu Val Ile Glu Lys Pro Glu Glu Gln Trp
145                 150                 155                 160

Trp Ser Ala Arg Asn Lys Asp Gly Arg Val Gly Met Ile Pro Val Pro
                165                 170                 175

Tyr Val Glu Lys Leu Val Arg Ser Ser Pro His Gly Lys His Gly Asn
            180                 185                 190
```

```
Arg Asn Ser Asn Ser Tyr Gly Ile Pro Glu Pro Ala His Ala Tyr Ala
    195             200             205

Gln Pro Gln Thr Thr Pro Leu Pro Ala Val Ser Gly Ser Pro Gly
    210             215             220

Ala Ala Ile Thr Pro Leu Pro Ser Thr Gln Asn Gly Pro Val Phe Ala
225             230             235             240

Lys Ala Ile Gln Lys Arg Val Pro Cys Ala Tyr Asp Lys Thr Ala Leu
                245             250             255

Ala Leu Glu Val Gly Asp Ile Val Lys Val Thr Arg Met Asn Ile Asn
            260             265             270

Gly Gln Trp Glu Gly Glu Val Asn Gly Arg Lys Gly Leu Phe Pro Phe
        275             280             285

Thr His Val Lys Ile Phe Asp Pro Gln Asn Pro Asp Glu Asn Glu
    290             295             300
```